(12) United States Patent
Kostik et al.

(10) Patent No.: US 7,745,436 B2
(45) Date of Patent: Jun. 29, 2010

(54) DISALT INHIBITORS OF IL-12 PRODUCTION

(75) Inventors: Elena Kostik, Arlington, MA (US); Lijun Sun, Harvard, MA (US)

(73) Assignee: Synta Pharmaceuticals Corporation, Lexington, MA (US)

( * ) Notice: Subject to any disclaimer, the term of this patent is extended or adjusted under 35 U.S.C. 154(b) by 114 days.

(21) Appl. No.: 11/105,818

(22) Filed: Apr. 13, 2005

(65) Prior Publication Data

US 2005/0282802 A1  Dec. 22, 2005

Related U.S. Application Data

(60) Provisional application No. 60/562,150, filed on Apr. 13, 2004.

(51) Int. Cl.
  *A61K 31/5377* (2006.01)
  *C07D 295/096* (2006.01)
(52) U.S. Cl. .................................. 514/235.8; 544/109
(58) Field of Classification Search ............. 514/235.8; 544/123, 109
  See application file for complete search history.

(56) References Cited

U.S. PATENT DOCUMENTS

| 6,384,032 | B1 | 5/2002 | Ono et al. |
| 6,680,315 | B2 | 1/2004 | Ono et al. |
| 6,693,097 | B2 | 2/2004 | Ono et al. |
| 6,858,606 | B2 | 2/2005 | Sun et al. |
| 7,045,517 | B2 | 5/2006 | Ono et al. |
| 7,067,514 | B2 | 6/2006 | Ono et al. |
| 7,465,725 | B2 | 12/2008 | Ono et al. |
| 7,470,681 | B2 | 12/2008 | Sun et al. |
| 7,470,685 | B2 | 12/2008 | Sun et al. |

FOREIGN PATENT DOCUMENTS

WO  WO 2004/035740 A2  4/2004

OTHER PUBLICATIONS

King, Med Chem: Principle and Practice (1994), p. 206-208.*
International Search Report in PCT International Application No. PCT/US05/12578.

\* cited by examiner

*Primary Examiner*—Taofiq A Solola
(74) *Attorney, Agent, or Firm*—Edwards Angell Palmer & Dodge LLP; Jeffrey D. Hsi; Mark D. Russett

(57) ABSTRACT

This invention relates to disalt nitrogen-heteroaryl inhibitors of IL-12 production, and related methods and pharmaceutical compositions.

6 Claims, No Drawings

DISALT INHIBITORS OF IL-12 PRODUCTION

RELATED APPLICATIONS

This application claims the benefit of U.S. Provisional Application No. 60/562,150, filed on Apr. 13, 2004, the entire teachings of which are incorporated herein by reference.

TECHNICAL FIELD

This invention relates to disalt inhibitors of IL-12 production, and related methods and pharmaceutical compositions.

BACKGROUND

Interleukin-12 (IL-12) is a heterodimeric cytokine (p70) which plays key roles in immune responses by bridging innate resistance and antigen-specific adaptive immunity. Trinchieri (1993) *Immunol Today* 14:335. For example, it promotes type 1 T helper cell ($T_H1$) responses and, hence, cell-mediated immunity. Chan et al. (1991) *J Exp Med* 173: 869; Seder et al. (1993) *Proc Natl Acad Sci USA* 90: 10188; Manetti et al. (1993) *J Exp Med* 177:1199; and Hsieh et al. (1993) *Science* 260: 547. Interleukin-12 (IL-12) is a disulfide linked heterodimeric cytokine composed of two independently regulated subunits, p35 and p40. IL-12 is produced by phagocytic cells and antigen presenting cells, in particular, macrophages and dendritic cells, upon stimulation with bacteria, bacterial products such as lipopolysaccharide (LPS), and intracellular parasites. The well-documented biological functions of IL-12 are induction of interferon-γ expression from T and NK cells and differentiation toward the $T_H1$ T lymphocyte type. IFN-γ, expression of which is induced by IL-12, is a strong and selective enhancer of IL-12 production from monocytes and macrophages. The cytokine IL-23 is a heterodimer composed of a p19 subunit and the same p40 subunit of IL-12. IL-23, similarly to IL-12, is involved in type 1 immune defenses and induces IFN-γ secretion from T cells. IL-27 is formed by the association of EBI3, a polypeptide related to the p40 subunit of IL-12, and p28, a protein related to the p35 subunit of IL-12. IL-27 promotes the growth of T cells and is thought to play a role in the differentiation of $T_H1$ cells. Pflanz et al., *Immunity* (2002), 16:779-790.

It has been suggested that, particularly in chronic diseases in which there is ongoing production of IFN-γ, IL-12 production is augmented by IFN-γ. It is presumed that after an infective or inflammatory stimulus that provokes IL-12 production, the powerful feedback loop promotes IL-12- and IL-23-induced IFN-γ to further augment IL-12 production, leading to consequent excessive production of pro-inflammatory cytokines. Furthermore, it has been suggested that IL-27 induces the expression of T-bet, a major $T_H1$-specific transcription factor, and it's downstream target IL-12R β2, independently of IFN-γ. In addition, IL-27 suppresses the expression of GATA-3. GATA-3 inhibits $T_H1$ development and causes loss of IL-12 signaling through suppression of IL-12R β2 and Stat4 expression. Lucas et al., *PNAS* (2003), 100: 15047-15052.

IL-12 plays a critical role in multiple-$T_H1$ dominant autoimmune diseases including, but not limited to, multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease. See, for example, Gately et al. (1998) *Annu Rev Immunol*. 16: 495; and Abbas et al. (1996) *Nature* 383: 787.

Inhibiting IL-12 overproduction, or inhibiting the production of cytokines such as IL-23 and IL-27 which promote IL-12 production and/or $T_H1$ development is an approach to treating the just-mentioned diseases. Trembleau et al. (1995) *Immmunol. Today* 16:383; and Adorini et al. (1997) *Chem. Immunol*. 68: 175. For example, overproduction of IL-12 and the resultant excessive $T_H1$ type responses can be suppressed by modulating IL-12, IL-23 and/or IL-27 production. Therefore, compounds that down-regulate IL-12, IL-23 and/or IL-27 production can be used for treating inflammatory diseases. Ma et al. (1998) *Eur Cytokine Netw* 9: 54.

IL-12 also plays a role in bone loss diseases, particularly those involving osteoclasts. Osteoclasts are unique multinucleated cells within bone that are responsible for bone degradation and resorption. These are the only cells in the body known to be capable of this function. Osteoclasts have a high capacity for the synthesis and storage of enzymes, including acid hydrolases and carbonic anhydrase isoenzyme II. Osteoclasts share phenotypic characteristics with circulating monocytes and tissue macrophages (N. Kurihara et al., *Endocrinology* 126: 2733-41 (1990); G. Hattersley et al, *Endocrinology* 128: 259-62 (1991)). These cells are derived from mononuclear precursors that are the progeny of stem-cell populations located in the bone marrow, spleen, and liver. Proliferation of these stem-cell populations produces osteoclastic precursors, which migrate via vascular routes to skeletal sites. These cells then differentiate. and fuse with each other to form osteoclasts, or alternatively, fuse with existing osteoclasts.

The regulation of osteoclastic formation and activity is only partly understood but it is known that excessive bone resorption by osteoclasts contributes to the pathology of many human diseases associated with excessive bone loss, including periodontal disease, non-malignant bone disorders (such as osteoporosis, Paget's disease of bone, osteogenesis imperfecta, fibrous dysplasia, and primary hyperparathyroidism) estrogen deficiency, inflammatory bone loss, bone malignancy, arthritis, osteopetrosis, and certain cancer-related disorders (such as hypercalcemia of malignancy (HCM), osteolytic bone lesions of multiple myeloma and osteolytic bone metastases of breast cancer and other metastatic cancers).

SUMMARY

This invention relates to disalt nitrogen-heteroaryl inhibitors of IL-12 production, and related methods of making and using such compounds, and pharmaceutical compositions thereof.

In one aspect, the invention relates to a disalt represented by formula (I):

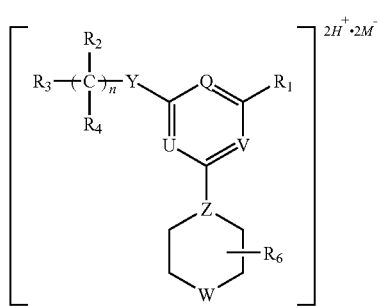

or a pharmaceutically acceptable solvate, clathrate, or prodrug thereof, wherein:

$R^1$ is

—X⁝⁝⁝[N⁝⁝⁝]$_t$B;

X is $C(R^c)$, O, S, S(O), S(O$_2$), or $NR^c$;
t is 0 or 1;
each of

⁝⁝⁝ and ⁝⁝⁝ is, independently a single or double bond;

B is substituted or unsubstituted aryl, substituted or unsubstituted heteroaryl, $C(R^a)(R^b)$, or L-B';

each of $R_2$ and $R_4$, independently, is $R^c$, halogen, nitro, cyano, azide, isothionitro, $SR^c$, or $OR^c$; or $R_2$ and $R_4$, taken together, is =O;

$R_3$ is $R^c$, halogen, CN, alkenyl, alkynyl, $OR^c$, $OC(O)R^c$, $SO_2R^c$, $S(O)R^c$, $S(O_2)NR^cR^d$, $SR^c$, $NR^cR^d$, $NR^cCOR^d$, $NR^c$-$C(O)OR^d$, $NR^cC(O)NR^cR^d$, $NR^cSO_2R^d$, $COR^c$, $C(O)OR^c$, or $C(O)NR^cR^d$;

$R_6$ is H, alkyl, $R^c$, halogen, nitro, cyano, azide, isothionitro, $SR^c$, or $OR^c$;

n is 0, 2, 3, 4, 5, 6, or 7;

Y is a covalent bond, $CH_2$, C(O), C=N—$R^c$, C=N—$OR^c$, C=N—$SR^c$, O, S, S(O), S(O)$_2$, or $NR^c$;

Z is N or CH;

each of Q, U and V is, independently, N or $CR^c$, provided that at least one of Q, U, and V is N;

W is O, S, S(O), S(O)$_2$, $NR^c$, or $NC(O)R^c$;

L is O, S, S(O), S(O)$_2$, $C(CR^c)_2$, or $NR^c$;

B' is substituted or unsubstituted aryl or substituted or unsubstituted heteroaryl;

each of $R^a$ and $R^b$ is, independently, hydrogen, an optionally substituted alkyl, an optionally substituted aryl, or an optionally substituted heteroaryl;

each of $R^c$ and $R^d$, independently, is H, an optionally substituted alkyl, an optionally substituted aryl, an optionally substituted aralkyl, an optionally substituted heteroaryl, an optionally substituted heteroaralkyl, an optionally substituted cyclyl, an optionally substituted heterocyclyl, or an alkylcarbonyl; and each $M^-$ is a conjugate base of a Bronsted acid.

In one embodiment, the invention relates to a disalt represented by formula (I), wherein each of Q, U and V is, independently, N or CH, provided that at least one of Q, U, and V is N.

In another embodiment, the invention relates to a disalt represented by formula (I) wherein Q, U, and V each are N.

In another embodiment, the invention relates to a disalt represented by formula (I) wherein two of Q, U and V are N, and the other is CH.

In another embodiment, the invention relates to a disalt represented by formula (I) wherein Q and U each are N and V is CH.

In another embodiment, the invention relates to a disalt represented by formula (I) wherein U and V are N, and Q is CH.

In another embodiment, the invention relates to a disalt represented by formula (I) wherein Q and V are N and U is CH.

In another embodiment, the invention relates to a disalt represented by formula (I) wherein one of Q, U and V is N, and the other two are each CH.

In another embodiment, the invention relates to a disalt represented by formula (I) wherein U is N and Q and V each are CH.

In another embodiment, the invention relates to a disalt represented by formula (I) wherein Q is N and U and V each are CH.

In another embodiment, the invention relates to a disalt represented by formula (I) wherein V is N and Q and U each are CH.

In another embodiment, the invention relates to a disalt represented by formula (I) wherein Y is a covalent bond, O, S, NH or $CH_2$, and n is 0, 1, 2, 3, or 4.

In another embodiment, the invention relates to a disalt represented by formula (I) wherein $R_2$ and $R_4$ each are hydrogen.

In another embodiment, the invention relates to a disalt represented by formula (I) wherein $R_3$ is optionally substituted aryl or optionally substituted heteroaryl.

In another embodiment, the invention relates to a disalt represented by formula (I) wherein $R_3$ is optionally substituted heteroaryl.

In another embodiment, the invention relates to a disalt represented by formula (I) wherein $R_3$ is pyridinyl.

In another embodiment, the invention relates to a disalt represented by formula (I) wherein $R_3$ is $OR^c$, $SR^c$, $C(O)OR^c$, $NR^cR^d$, or $C(O)NR^cR^d$.

In another embodiment, the invention relates to a disalt represented by formula (I) wherein $R_3$ is optionally substituted heterocyclyl.

In another embodiment, the invention relates to a disalt represented by formula (I) wherein $R_3$ is morpholino.

In another embodiment, the invention relates to a disalt represented by formula (I) wherein $R^3$ is heteroaryl, heterocyclyl, or $NR^cR^d$, wherein each of $R^c$ and $R^d$ of $NR^cR^d$ is, independently, hydrogen, alkyl, cyclyl, or heterocyclyl.

In another embodiment, the invention relates to a disalt represented by formula (I) wherein $R_3$ is

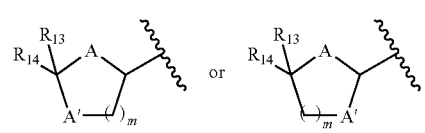

wherein:

each of A and A', independently, is O, S, S(O), S(O)$_2$, or NH;

each of $R_{13}$ and $R_{14}$, independently is H, optionally substituted alkyl, optionally substituted aryl, or optionally substituted heteroaryl; and m is 1 or 2.

In another embodiment, the invention relates to a disalt represented by formula (I) wherein Z is N and W is O.

In another embodiment, the invention relates to a disalt represented by formula (I) wherein t is 0, and

⁝⁝⁝⁝ is a single bond.

In another embodiment, the invention relates to a disalt represented by formula (I) wherein X is —NH— or —N(CH$_3$)—.

In another embodiment, the invention relates to a disalt represented by formula (I) wherein t is 0,

⁝⁝⁝⁝ is a single bond, and X is —NH— or —N(CH$_3$)—.

In another embodiment, the invention relates to a disalt represented by formula (I) wherein B is:

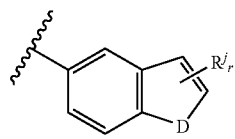

wherein:

D is O, S, S(O), S(O)$_2$, or NR$^m$;

R$^j$, for each occurrence, is independently, halogen, CN, hydroxyl, alkyl, optionally substituted aryl, optionally substituted heteroaryl, alkoxyl, optionally substituted aryloxyl, or optionally substituted heteroaryloxyl; or two R$^j$ attached to two consecutive carbons together form a fused benzene ring;

R$^m$ is H, alkyl, or alkylcarbonyl; and r is 0, 1, or 2.

In another embodiment, the invention relates to a disalt represented by formula (I) wherein B is optionally substituted aryl.

In another embodiment, the invention relates to a disalt represented by formula (I) wherein B is naphthyl or

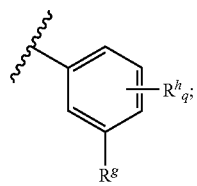

wherein:

R$^g$ is H, halogen, CN, alkyl, cyclyl, alkyloxy, alkylcarbonyl, alkyloxycarbonyl, aryloxycarbonyl, heteroaryloxycarbonyl, hydroxyalkyl, alkylamino, or alkylaminocarbonyl;

R$^h$, for each occurrence, is independently, halogen, NO$_2$, CN, alkyl, aryl, heteroaryl, OR$^c$, OC(O)R$^c$, SO$_2$R$^c$, S(O)R$^c$, S(O)$_2$NR$^c$R$^d$, SR$^c$, NR$^c$R$^d$, NR$^c$C(O)OR$^d$, NR$^c$C(O)OR$^d$, NR$^c$C(O)NR$^c$R$^d$, NR$^c$C(NR)NR$^c$R$^d$, NR$^c$SO$_2$R$^d$, C(O)R$^c$, OC(O)R$^c$, C(O)OR$^c$, or C(O)NR$^c$R$^d$;

R is an alkyl, an aryl, an aralkyl, —C(O)R$^c$, —OR$^c$, —SR$^c$, —NR$^c$R$^d$, hydroxylalkyl, nitro, cyano, haloalkyl, aminoalkyl, or —S(O)$_2$R$^c$;

q is 0, 1, 2, 3, or 4.

In another embodiment, the invention relates to a disalt represented by formula (I) wherein R$^3$ is heteroaryl, heterocyclyl, or NR$^c$R$^d$, wherein each of R$^c$ and R$^d$ of NR$^c$R$^d$ is, independently, hydrogen, alkyl, cyclyl, or heterocyclyl.

In another embodiment, the invention relates to a disalt represented by formula (I) wherein t is 1.

In another embodiment, the invention relates to a disalt represented by formula (I) wherein X is NR$^c$,

⁝⁝⁝⁝ is a single bond,

⁝⁝⁝⁝ is a double bond, t is 1, and B is C(R$^a$)(R$^b$).

In another embodiment, the invention relates to a disalt represented by formula (I) wherein X is —NH— or —N(CH$_3$)—.

In another embodiment, the invention relates to a disalt represented by formula (I) wherein one of R$^a$ and R$^b$ is

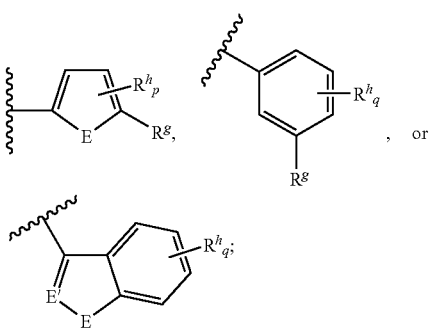

wherein:

E is NR$^i$, O, S, S(O), or S(O)$_2$;

E' is N or CR$^i$;

R$^i$ is H, alkyl, or alkylcarbonyl;

R$^g$, R$^h$, p and q are defined as above.

In another embodiment, the invention relates to a disalt represented by formula (I) wherein one of R$^a$ and R$^b$ is

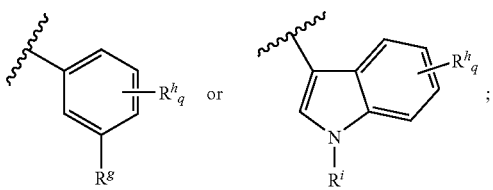

and the other of $R^a$ and $R^b$ is H or alkyl, wherein:

$R^g$, $R^h$, $R^i$, and q are as defined above. In another aspect of this embodiment, $R^g$ is H, methyl, ethyl, propyl, cyclopropyl, methoxy, ethoxy, methoxycarbonyl, or halogen; $R^h$ is F, Cl, CN, methyl, methoxy, ethoxy, $OC(O)CH_3$, $OC(O)C_2H_5$, $C(O)OH$, $C(O)OC_2H_5$, $C(O)NH_2$, $NHC(O)CH_3$, or $S(O)_2NH_2$; $R^i$ is H, methyl, ethyl, or acetyl; and q is 0, 1, or 2.

In another embodiment, the invention relates to a disalt represented by formula (I) wherein one of $R^a$ and $R^b$ is:

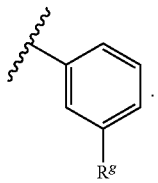

and the other of $R^a$ and $R^b$ is H or alkyl, wherein $R^g$ is defined as above. In another aspect of this embodiment, $R^g$ is halogen, an alkyl or an alkyloxycarbonyl.

In another embodiment, the invention relates to a disalt represented by formula (I) wherein X is $C(R^c)$,

:::::

is a double bond,

⋯ is a single bond, and B is L-B'.

In another embodiment, the invention relates to a disalt represented by formula (I) wherein L is —NH— or —N(CH$_3$)—.

In another embodiment, the invention relates to a disalt represented by formula (I) wherein X is CH;

In another embodiment, the invention relates to a disalt represented by formula (I) wherein B' is:

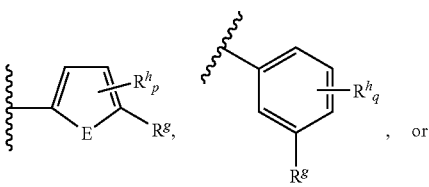

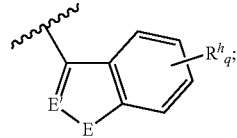

wherein E, E', $R^g$, $R^h$, p, and q are defined as above.

In another embodiment, the invention relates to a disalt represented by formula (I) wherein B' is wherein $R^g$, $R^h$, and q are defined as above.

One or more embodiments of for the compounds represented by formulas (I) may be combined to form additional compounds of the invention. All such combinations are expressly encompassed in this invention.

In another aspect, the invention relates to a disalt represented by formula (II):

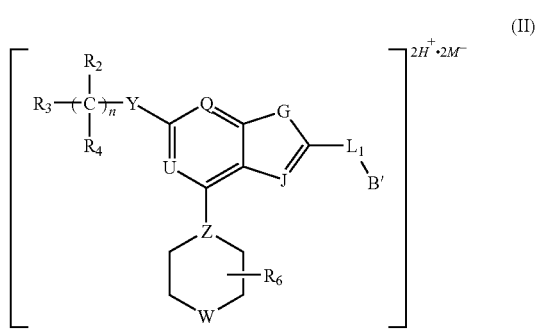

or a pharmaceutically acceptable solvate, clathrate, or prodrug thereof, wherein B', M⁻, Q, U, W, Y, Z, $R_2$, $R_3$, $R_4$, $R_6$, and n are defined as above; and wherein:

G is O, S, S(O), $S(O)_2$, or $NR^e$;
$L_1$ is O, S, S(O), $S(O)_2$, $NR^e$, or C(O);
J is N or $CR^f$;
$R^e$, for each occurrence, is independently, H, alkyl, aryl, acyl, arylsulfonyl, or alkylsulfonyl; and
$R^f$ is H, alkyl, aryl, acyl, arylsulfonyl, alkylsulfonyl, alkoxyl, amino, ester, amide, CN, or halogen.

In one embodiment, the invention relates to a disalt represented by formula (II) wherein G is $NR^e$, and J is N.

In another embodiment, the invention relates to a disalt represented by formula (II) wherein Z is N.

In another embodiment, the invention relates to a disalt represented by formula (II) wherein W is O.

In another embodiment, the invention relates to a disalt represented by formula (II) wherein $L_1$ is $NR^e$.

In another embodiment, the invention relates to a disalt represented by formula (II) wherein each of Q and U is N.

In another embodiment, the invention relates to a disalt represented by formula (II) wherein $R_3$ is a halogen, CN, an alkyl, an aryl, a heteroaryl, OR$^c$, OC(O)R$^c$, NR$^c$R$^d$, NRC$^c$(O)R$^d$, C(O)OR$^c$, or C(O)NR$^d$R$^d$.

In another embodiment, the invention relates to a disalt represented by formula (II) wherein R$_3$ is optionally substituted aryl, optionally substituted heteroaryl, optionally substituted aryloxyl, or optionally substituted heteroaryloxyl.

In another embodiment, the invention relates to a disalt represented by formula (II) wherein R$_3$ is optionally substituted heteroaryl.

In another embodiment, the invention relates to a disalt represented by formula (II) wherein R$_3$ is pyridinyl, triazolyl, tetrazolyl, pyrimidinyl, thiazolyl, indolyl, or indolizinyl.

In another embodiment, the invention relates to a disalt represented by formula (II) wherein the compound is an N-oxide.

In another embodiment, the invention relates to a disalt represented by formula (II) wherein B' is an optionally substituted aryl.

In another embodiment, the invention relates to a disalt represented by formula (II) wherein Y is NR$^c$.

In another embodiment, the invention relates to a disalt represented by formula (II) wherein Y is O.

In another embodiment, the invention relates to a disalt represented by formula (II) wherein B' is

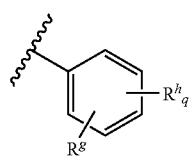

wherein R$^g$, R$^h$, and q are defined as above.

In another embodiment, the invention relates to a disalt represented by formula (II) wherein B' is

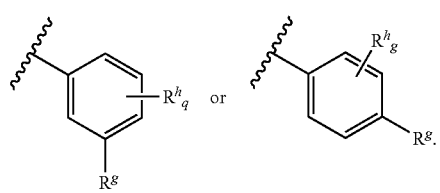

wherein R$^g$, R$^h$, and q are defined as above. In another aspect of this embodiment, R$^g$ is H, F, Cl, Br, I, CN, Me, Et, Pr, i-Pr, OMe, or OEt.

One or more embodiments of for the compounds represented by formulas (II) may be combined to form additional compounds of the invention. All such combinations are expressly encompassed in this invention.

In another aspect, the invention relates to a disalt represented by formula (III):

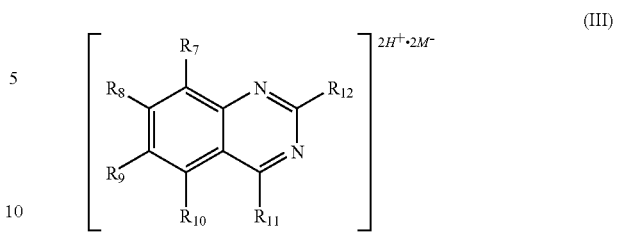

(III)

or a pharmaceutically acceptable solvate, clathrate, or prodrug thereof, wherein:

each of R$_7$, R$_8$, R$_9$, and R$_{10}$, independently, is R$^c$, halogen, CN, alkenyl, alkynyl, OR$^c$, OC(O)R$^c$, SO$_2$R$^c$, S(O)R$^c$, S(O$_2$)NR$^c$R$^d$, SR$^c$, NR$^c$R$^d$, NR$^c$COR$^d$, NR$^c$C(O)OR$^d$, NR$^c$C(O)NR$^c$R$^d$, NR$^c$SO$_2$R$^d$, COR$^c$, C(O)OR$^c$, or C(O)NR$^c$R$^d$;

one of R$_{11}$ and R$_{12}$ is -L$_2$-R$_5$ and the other is a group represented by the following structural formula:

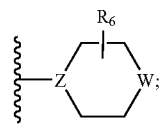

R$_5$ is an optionally substituted aryl, an optionally substituted heteroaryl or a group represented by the following formula:

L$_2$ is O, S, S(O), S(O)$_2$, or NR$^c$; and

M$^-$, W, Z, R$^a$, R$^b$, R$^c$, R$^d$, and R$_6$ are defined as above.

In one embodiment, the invention relates to a disalt represented by formula (III) wherein R$_5$ is represented by the following formula:

In another embodiment, the invention relates to a disalt represented by formula (III) wherein L$_2$ is —NH—, —N(CH$_3$)—, —N(CH$_2$CH$_3$)—, or —N(C(O)CH$_3$)—.

In another embodiment, the invention relates to a disalt represented by formula (III) wherein Z is N and W is O.

In another embodiment, the invention relates to a disalt represented by formula (III) wherein one of R$^a$ and R$^b$ is an optionally substituted aryl or an optionally substituted heteroaryl, and the other of R$^a$ and R$^b$ is H or alkyl.

In another embodiment, the invention relates to a disalt represented by formula (III) wherein each of R$_7$, R$_8$, R$_9$, and R$_{10}$, independently, is H, —OH, an alkoxy, or an alkylcarbonyl.

In another embodiment, the invention relates to a disalt represented by formula (III) wherein one of R$^a$ and R$^b$ is

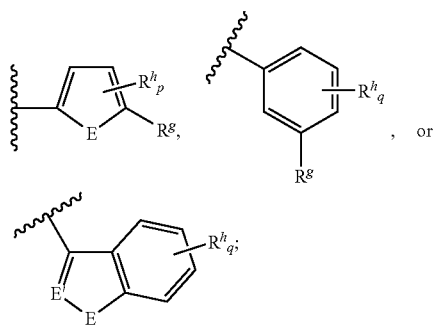

wherein E, E', $R^g$, $R^h$, p and q are defined as above.

In another embodiment, the invention relates to a disalt represented by formula (III) wherein one of $R^a$ and $R^b$ is a group represented by the following structural formula:

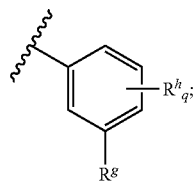

wherein $R^g$, $R^h$ and q are defined as above; and the other of $R^a$ and $R^b$ is H or alkyl. In another aspect of this embodiment, $R^g$ is H, methyl, ethyl, propyl, cyclopropyl, methoxy, or ethoxy; and $R^h$, for each occurrence, is independently, F, Cl, CN, methyl, methoxy, ethoxy, $OC(O)CH_3$, $OC(O)C_2H_5$, $C(O)OH$, $C(O)OC_2H_5$, $C(O)NH_2$, $NHC(O)CH_3$, or $S(O_2)NH_2$. In another aspect of this embodiment, $R^g$ is methyl or methoxy.

In another embodiment, the invention relates to a disalt represented by formula (III) wherein Z is N and W is O.

In another embodiment, the invention relates to a disalt represented by formula (III) wherein $L_2$ is —NH—, —N($CH_3$)—, —N($CH_2CH_3$)—, or —N(C(O)$CH_3$).

In another embodiment, the invention relates to a disalt represented by formula (III) wherein each of $R_7$, $R_8$, $R_9$, and $R_{10}$, independently, is H, —OH, an alkoxy, or an alkylcarbonyl.

In another embodiment, the invention relates to a disalt represented by formula (III) wherein each of $R_7$ and $R_{10}$ is H and each of $R_8$ and $R_9$ is $OCH_3$.

In another embodiment, the invention relates to a disalt represented by formula (III) wherein $R_6$ is H.

In another embodiment, the invention relates to a disalt represented by formula (III) wherein $R_{12}$ is a group represented by the following structural formula:

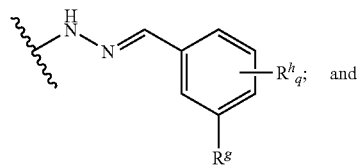

$R_{11}$ is a group represented by the following formula:

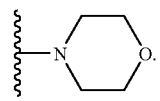

In another embodiment, the invention relates to a disalt represented by formula (III) wherein $R_{12}$ is a group represented by the following structural formula:

$R_{11}$ is a group represented by the following structural formula:

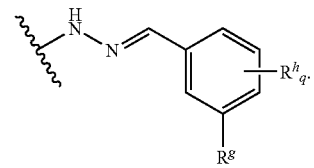

In another embodiment, the invention relates to a disalt represented by formula (III) wherein $R_5$ is an optionally substituted aryl or an optionally substituted heteroaryl.

In another embodiment, the invention relates to a disalt represented by formula (III) wherein $R_5$ is:

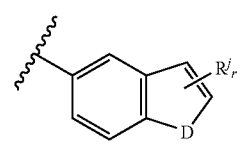

wherein D, $R^j$, and r are defined as above. In one aspect of this embodiment, r is 1 or 2; and each $R^j$ is, independently, methyl, ethyl, or propyl; or two $R^j$ attached to two consecutive carbons together form a fused benzene ring.

In another embodiment, the invention relates to a disalt represented by formula (III) wherein $R_5$ is a group represented by the following structural formula:

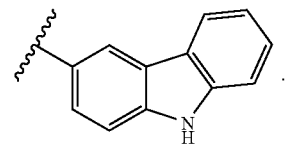

In another embodiment, the invention relates to a disalt represented by formula (III) wherein each of $R_7$, $R_8$, $R_9$, and $R_{10}$, independent, is H or $OR^c$.

In another embodiment, the invention relates to a disalt represented by formula (III) wherein $R_{12}$ is a group represented by the following structural formula:

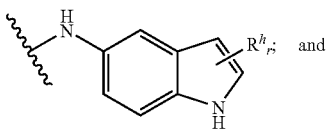

$R_{11}$ is a group represented by the following structural formula:

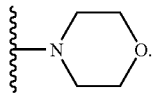

In another embodiment, the invention relates to a disalt represented by formula (III) wherein $R_{12}$ is a group represented by the following structural formula:

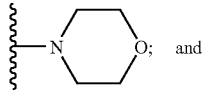

$R_{11}$ is a group represented by the following structural formula:

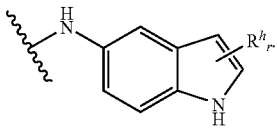

One or more embodiments of for the compounds represented by formulas (III) may be combined to form additional compounds of the invention. All such combinations are expressly encompassed in this invention.

In another embodiment, the invention relates to a disalt represented by formula (I), (II), or (III) wherein $M^-$ is the conjugate base of a Bronsted acid having a pKa in the range of between about −15 and about 5.

In another embodiment, the invention relates to a disalt represented by formula (I), (II), or (III) wherein $M^-$ is the conjugate base of a Bronsted acid having a pKa of at most about −6.

In another embodiment, the invention relates to a disalt represented by formula (I), (II), or (III) wherein $M^-$ is the conjugate base of a Bronsted acid having a pKa of at most about −1.

In another embodiment, the invention relates to a disalt represented by formula (I), (II), or (III) wherein $M^-$ is the conjugate base of a Bronsted acid having a pKa of at most about 1.

In another embodiment, the invention relates to a disalt represented by formula (I), (II), or (III) wherein $M^-$ is methanesulfonate.

In another embodiment, the invention relates to a disalt represented by formula (I), (II), or (III) wherein $M^-$ is bromide.

In another embodiment, the invention relates to a disalt represented by formula (I), (II), or (III) wherein $M^-$ is chloride.

In another embodiment, the invention relates to a disalt represented by formula (I), (II), or (III) wherein $M^-$ is any combination of the aforementioned conjugate bases of a Bronsted acid.

Another aspect of the invention is a product (e.g., compound or composition) made by a process as delineated herein. The process can include one or more chemical transformations, salt formation, or other chemical process as delineated herein; and can include one or more reagents, intermediates, solvents, or conditions, as delineated herein.

In another aspect, the present invention features a method for treating or preventing an IL-12 production-related disorder such as multiple sclerosis, sepsis, myasthenia gravis, autoimmune neuropathies, Guillain-Barre syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease. The method involves administering to a subject (e.g., a human or an animal) in need of treatment for an IL-12 production-related disorder an effective amount of one or more disalts described herein, or a pharmaceutically acceptable solvate, clathrate, or prodrug thereof, or a pharmaceutical composition comprising an effective amount of one or more disalts described herein, or a pharmaceutically acceptable solvate, clathrate, or prodrug thereof. In one embodiment, the method involves treating or preventing an IL-12 production-related disorder selected from the group consisting of rheumatoid arthritis, sepsis, Crohn's disease, multiple sclerosis, psoriasis, or immune-mediated diabetes mellitus. The identification of a subject in need of treatment for an IL-12 production-related disorder can be in the judgment of the subject or a health professional and can be subjective (e.g., opinion) or objective (e.g., measurable by a test or a diagnostic method).

In one aspect, this invention features a method for treating or preventing disorders associated with excessive bone loss, e.g., periodontal disease, non-malignant bone disorders (e.g., osteoporosis, Paget's disease of bone, osteogenesis imperfecta, fibrous dysplasia, and primary hyperparathyroidism), estrogen deficiency, inflammatory bone loss, bone malignancy, arthritis, osteopetrosis, and certain cancer-related disorders (e.g., hypercalcemia of malignancy (HCM), osteolytic bone lesions of multiple myeloma and osteolytic bone metastases of breast cancer and other metastatic cancers). The method includes administering to a subject (e.g., a human or an animal) in need thereof an effective amount of one or more disalts described herein or a pharmaceutically acceptable solvate, clathrate, or prodrug thereof, or a pharmaceutical composition comprising an effective amount of one or more disalts described herein or a pharmaceutically acceptable solvate, clathrate, or prodrug thereof. The method can also include the step of identifying that the subject is in need of treatment of diseases or disorders described above. The identification can be in the judgment of a subject or a health professional and can be subjective (e.g., opinion) or objective (e.g., measurable by a test or a diagnostic method).

In another aspect, this invention features methods for inhibiting osteoclast formation in vitro or in vivo. The method includes contacting a pre-osteoclast cell (e.g., a cell capable of forming an osteoclast cell upon differentiation and/or fusion) with an effective amount of a disalt described herein or a pharmaceutically acceptable solvate, clathrate, or prodrug thereof or a pharmaceutical composition comprising an effective amount of a disalt described herein or a pharmaceutically acceptable solvate, clathrate, or prodrug thereof.

In a further aspect, this invention features methods of treating or preventing a disorder associated with excessive bone resorption by osteoclasts in a subject in need thereof. The method includes administering to a subject (e.g., a human or an animal) in need thereof an effective amount of one or more disalts described herein or a pharmaceutically acceptable solvate, clathrate, or prodrug thereof, or a pharmaceutical composition comprising an effective amount of one or more disalts described herein or a pharmaceutically acceptable solvate, clathrate, or prodrug thereof. The method can also include the step of identifying that the subject is in need of treatment of diseases or disorders described above. The identification can be in the judgment of a subject or a health professional and can be subjective (e.g., opinion) or objective (e.g., measurable by a test or a diagnostic method).

The disalts of this invention can include the diprotonated IL-12 production inhibitor compounds themselves, as well as their prodrugs, if applicable. As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "pharmaceutically acceptable solvate," is a solvate formed from the association of one or more solvent molecules to one of the disalts of this invention. The term solvate includes hydrates (e.g., hemi-hydrate, monohydrate, dihydrate, trihydrate, tetrahydrate, and the like).

The disalts of this invention may contain one or more asymmetric centers and thus occur as racemates and racemic mixtures, single enantiomers, individual diastereomers and diastereomeric mixtures. All such isomeric forms of these disalts are expressly included in the present invention. The disalts of this invention may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The disalts of this invention may also be represented in multiple tautomeric forms, in such instances, the invention expressly includes all tautomeric forms of the disalts described herein, even though only a single tautomeric form may be represented (e.g., alkylation of a ring system may result in alkylation at multiple sites, the invention expressly includes all such reaction products). All such isomeric forms of such disalts are expressly included in the present invention. All crystal forms and polymorphs of the disalts described herein are expressly included in the present invention.

Further, the aforementioned aromatic ring nitrogen-containing compounds also include their N-oxides. The term "N-oxides" refers to one or more nitrogen atoms, when present in an aromatic ring nitrogen-containing compound, are in N-oxide form, i.e., N→O.

Combinations of substituents and variables envisioned by this invention are only those that result in the formation of stable disalts. The term "stable", as used herein, refers to disalts, which possess stability sufficient to allow manufacture and which maintains the integrity of the disalt for a sufficient period of time to be useful for the purposes detailed herein (e.g., treating IL-12 production-related disorders such as rheumatoid arthritis, sepsis, Crohn's disease, multiple sclerosis, psoriasis, or insulin-dependent diabetes mellitus, treating or preventing disorders associated with excessive bone loss, e.g., periodontal disease, non-malignant bone disorders (e.g., osteoporosis, Paget's disease of bone, osteogenesis imperfecta, fibrous dysplasia, and primary hyperparathyroidism) estrogen deficiency, inflammatory bone loss, bone malignancy, arthritis, osteopetrosis, and certain cancer-related disorders (e.g., hypercalcemia of malignancy (HCM), osteolytic bone lesions of multiple myeloma and osteolytic bone metastases of breast cancer and other metastatic cancers), inhibiting osteoclast formation in vitro or in vivo, or treating or preventing a disorder associated with excessive bone resorption by osteoclasts.).

Also within the scope of this invention are a composition comprising a pharmaceutically acceptable carrier and one or more of the disalts described above. The compositions may be used for treating an IL-12 production-related disorder (e.g., rheumatoid arthritis, sepsis, Crohn's disease, multiple sclerosis, psoriasis, or insulin-dependent diabetes mellitus), treating or preventing disorders associated with excessive bone loss, e.g., periodontal disease, non-malignant bone disorders (e.g., osteoporosis, Paget's disease of bone, osteogenesis imperfecta, fibrous dysplasia, and primary hyperparathyroidism) estrogen deficiency, inflammatory bone loss, bone malignancy, arthritis, osteopetrosis, and certain cancer-related disorders (e.g., hypercalcemia of malignancy (HCM), osteolytic bone lesions of multiple myeloma and osteolytic bone metastases of breast cancer and other metastatic cancers), inhibiting osteoclast formation in vitro or in vivo, or treating or preventing a disorder associated with excessive bone resorption by osteoclasts).

In another aspect, this invention features a pharmaceutical composition that contains a pharmaceutically acceptable carrier and an effective amount of at least one of the disalts of this invention, or a pharmaceutically acceptable solvate, clathrate, or prodrug thereof. These compositions may further include one or more additional active agents. The compositions are useful for treating or preventing one or more of the disorders delineated herein.

Also within the scope of the invention is the use of one or more disalts described herein, or a pharmaceutically acceptable solvate, clathrate, or prodrug thereof, or a pharmaceutical composition comprising an effective amount of one or more disalts described herein, or a pharmaceutically acceptable solvate, clathrate, or prodrug thereof, for the manufacture of a medicament. The medicament may be used for treating an IL-12 production-related disorder (e.g., rheumatoid arthritis, sepsis, Crohn's disease, multiple sclerosis, psoriasis, or insulin-dependent diabetes mellitus), treating or preventing disorders associated with excessive bone loss, e.g., periodontal disease, non-malignant bone disorders (e.g., osteoporosis, Paget's disease of bone, osteogenesis imperfecta, fibrous dysplasia, and primary hyperparathyroidism) estrogen deficiency, inflammatory bone loss, bone malignancy, arthritis, osteopetrosis, and certain cancer-related disorders (e.g., hypercalcemia of malignancy (HCM), osteolytic bone lesions of multiple myeloma and osteolytic bone metastases of breast cancer and other metastatic cancers), inhibiting osteoclast formation in vitro or in vivo, or treating or preventing a disorder associated with excessive bone resorption by osteoclasts).

The invention also relates to a method of making a disalt described herein. In one embodiment, the method comprises contacting with a Bronsted acid having a pKa in the range of between about −1 5 and about 5, a compound represented by formula (Ia), (IIa) or (IIIa):

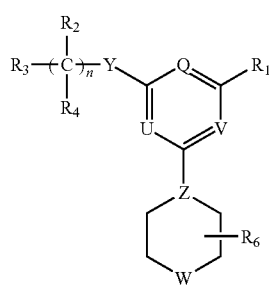

(Ia)

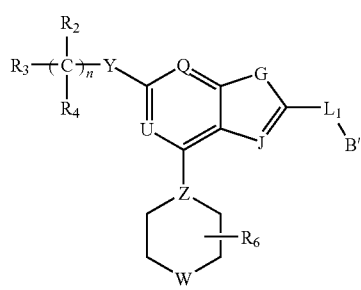

(IIa)

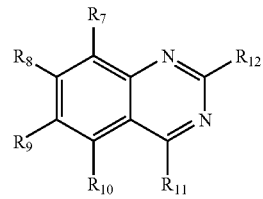

(IIIa)

wherein $R_1, R_2, R_3, R_4, R_6, R_7, R_8, R_9, R_{10}, R_{11}, R_{12}, B', G, J, L_1, Q, U, V, W, Y$, and n are defined as above.

In one embodiment, the method includes taking any one of the intermediate compounds described herein and reacting it with one or more chemical reagents in one or more steps to produce a compound described herein.

In some embodiments, the disalts have one or more properties that are enhanced relative to the corresponding monoprotonated compounds and/or the unprotonated compounds, e.g., bioavailability, solubility, melting point, and stability), and advantageously can have more optimal formulation properties relative to those of the monoprotonated compounds and/or the unprotonated compounds.

Other features and advantages of the invention will be apparent from the description and from the claims.

DETAILED DESCRIPTION

As used herein, the term "alkyl" refers to a straight-chained or branched hydrocarbon group containing 1 to 12 carbon atoms. Alkyl groups may be optionally substituted with one or more substituents. Examples of alkyl groups include methyl, ethyl, n-propyl, isopropyl, tert-butyl, and n-pentyl.

As used herein, the term "alkoxy" or "alkyloxy" refers to an alkyl group that is linked to another moiety by an oxygen (i.e., —O-alkyl). The alkyl portion of an alkoxy group may be optionally substituted.

The term "alkenyl" refers to an unsaturated hydrocarbon chain that may be a straight chain or branched chain containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "aryl" refers to a hydrocarbon monocyclic, bicyclic or tricyclic ring system having at least one aromatic ring. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "alkylene" refers to an alkyl group that has two points of attachment. The term "$(C_1$-$C_6)$alkylene" refers to an alkylene group that has from one to six carbon atoms. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like.

As used herein, the term "aralkyl" means an aryl group that is attached to another group by a ($C_1$-$C_6$)alkylene group. Aralkyl groups may be optionally substituted, either on the aryl portion of the aralkyl group or on the alkylene portion of the aralkyl group, with one or more substituent. Representative aralkyl groups include benzyl, 2-phenyl-ethyl, naphth-3-yl-methyl and the like.

The term "heteroaryl" refers to a mono-, bi- or tri-cyclic ring system having at least one aromatic ring, wherein a monocyclic heteroaryl has 5-8 members, a bicyclic heteroaryl has 8-12 members, and a tricyclic heteroaryl has 11-14 member. A heteroaryl may have 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, iso-quinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a ($C_1$-$C_6$)alkylene. Heteroaralkyl groups may be optionally substituted, either on the heteroaryl portion of the heteroaralkyl group or on the alkylene portion of the heteroaralkyl group, with one or more substituent. Representative heteroaralkyl groups include 2-(pyridin-4-yl)-propyl, 2-(thien-3-yl)-ethyl, imidazol-4-yl-methyl and the like.

The term "cyclyl" refers to a partially or fully saturated non-aromatic mono-cyclic or bi-cyclic hydrocarbon ring system having from 3 to 14 ring atoms. Exemplary cyclyl rings include cyclopropyl, cyclohexanyl, cyclopentanyl, cyclohexenyl, cyclohexadienyl, cyclopentenyl, and the like.

The term "heterocyclyl" refers to a partially or fully saturated non-aromatic mono-cyclic or bi-cyclic ring system having from 3 to 14 ring atoms. A heterocyclyl ring contains one or more heteroatoms (e.g., O, N, or S) as part of the ring system and the remainder being carbon. Exemplary heterocyclyl rings include piperidinyl, piperazinyl, morpholinyl, thiomorpholinyl, 1,4-oxazepanyl, pyranyl, 2-oxo-1H-pyridinyl, and the like.

The term "mercapto" refers to —SH. The term "alkyl sulfanyl" refers to —S-alkyl. The term "aryl sulfanyl" refers to —S-aryl. The alkyl or aryl portion of an alkyl sulfanyl or an aryl sulfanyl may be optionally substituted.

As used herein, the term "halogen" or "halo" means —F, —Cl, —Br or —I.

As used herein, the term "haloalkyl" means an alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, the term "haloalkoxy" means an alkoxy group in which one or more (including all) the hydrogen radicals are replaced by a halo group, wherein each halo group is independently selected from —F, —Cl, —Br, and —I.

The term "amino" refers to —$NH_2$. The term "alkylamino" refers to an amino group in which one hydrogen radical has been replaced by an alkyl group. The term "dialkylamino" refers to an amino group in which two hydrogen radicals have been replaced by two independently selected alkyl groups. Likewise, the term "arylamino" refers to an amino group in which one hydrogen radical has been replaced by an aryl group. The term "diarylamino" refers to an amino group in which two hydrogen radicals have been replaced by two independently selected aryl groups.

The term "azide" refers to a group having the formula —N=$N^+$=$N^-$

The term "mercaptoalkyl" refers to an alkyl substituent which is further substituted with one or more mercapto groups. The term "mercaptoalkoxy" refers to an alkoxy substituent which is further substituted with one or more mercapto groups.

The term "hydroxyalkyl" or "hydroxylalkyl" refers to an alkyl substituent which is further substituted with one or more hydroxyl groups.

The term "sulfonylalkyl" refers to an alkyl substituent which is further substituted with one or more sulfonyl groups. The term "sulfonylaryl" refers to an aryl substituent which is further substituted with one or more sulfonyl groups.

The term alkylcarbonyl refers to an —C(O)-alkyl. The term "alkylcarbonylalkyl" refers to an alkyl substituent which is further substituted with —C(O)-alkyl. The alkyl or aryl portion of alkylamino, dialkylamino, aminoalkyl, mercaptoalkyl, mercaptoalkoxy, hydroxyalkyl, mercaptoalkoxy, sulfonylalkyl, sulfonylaryl, alkylcarbonyl, and alkylcarbonylalkyl may be optionally substituted with one or more substituents.

The term "ester" refers to a —C(O)O—$R^e$; or, where a divalent group is indicated, an "ester" group is —C(O)O— or —OC(O)—. An "amido" is an —C(O)$NH_2$. A divalent "amide" group is indicated, the group is —C(O)N— or —NC(O)—.

An alkyl, alkoxy, alkyl sulfanyl, alkylamino, dialkylamino, alkylene, alkenyl, alkynyl, cyclyl, heterocyclyl, aryl, aralkyl, and heteroaryl mentioned above can be substituted or unsubstituted moieties. The term "substituted" refers to one or more substituents (which may be the same or different), each replacing a hydrogen atom. Suitable substituents for an alkyl, alkoxy, alkyl sulfanyl, alkylamino, dialkylamino, alkylene, alkenyl, alkynyl, cyclyl, heterocyclyl, aryl, aralkyl, and heteroaryl groups include any substituent which will form a stable compound of the invention. Examples of substituents for an alkyl, alkoxy, alkylsulfanyl, alkylamino, dialkylamino, alkylene, alkenyl, alkynyl, cycloalkyl, cycloalkenyl, heterocyclyl, aryl, aralkyl, heteroaryl, and heteroarylalkyl include an alkyl, alkoxy, alkyl sulfanyl, alkylamino, dialkylamino, an alkenyl, an alkynyl, an cycloalkyl, an cycloalkenyl, an heterocyclyl, an aryl, an heteroaryl, an aralkyl, an heteraralkyl, a haloalkyl, halo, cyano, nitro, haloalkoxy, —$OR_5$, —$SR_{15}$, —$NR_{17}R_{18}$, —$C(O)NR_{17}R_{18}$, —$NR_{15}C(O)R_{16}$, —$C(S)NR_{17}R_{18}$, —$NR_{15}C(S)R_{16}$, —$C(NR19)NR_{17}R_{18}$, —$NR_{15}C(NR_{19})R_{16}$, —$C(O)R_{15}$, —$C(S)R_{15}$, —$C(NR_{19})R_{15}$, —$C(O)OR_{15}$, —$C(O)SR_{15}$, —$OC(O)R_{15}$, —$SC(O)R_{15}$, —$C(S)OR_{15}$, —$C(S)SR_{15}$, —$OC(S)R_{15}$, —$SC(S)R_{15}$, —$C(NR_{19})$ $OR_{15}$, —$C(NR_{19})SR_{15}$, —$OC(NR_{19})R_{15}$, —$SC(NR_{19})R_{15}$, —$NR_{15}C(O)NR_{17}R_{18}$, —$NR_{15}C(S)NR_{17}R_{18}$, —$NR_{15}C(NR_{19})NR_{17}R_{18}$, —$OC(O)NR_{17}R_{18}$, —$OC(S)NR_{17}R_{18}$, —$OC(NR_{19})NR_{17}R_{18}$, —$SC(O)NR_{17}R_{18}$, —$SC(S)NR_{17}R_{18}$, —$SC(NR_{19})NR_{17}R_{18}$, —$NR_{15}C(O)OR_{16}$, —$NR_{15}C(S)OR_{16}$, —$NR_{15}C(NR_{19})OR_{16}$, —$NR_{15}C(O)SR_{16}$, —$NR_{15}C(S)SR_{16}$, —$NR_{15}C(NR_{19})SR_{16}$, —$S(O)_pOR_{15}$, —$OS(O)_pOR_{15}$, —$OS(O)_pR_{15}$, —$S(O)_pR_{15}$, —$S(O)_pNR_{17}R_{18}$, —$NR_{15}S(O)_pR_{16}$, —$P(O)(OR_{15})_2$, —$OP(O)(OR_{15})_2$, —$P(S)(OR_{15})_2$, —$OP(S)(OR_{15})_2$, —$SP(O)(OR_{15})_2$, —$OP(O)(OR_{15})(SR_{16})$, or —$P(O)(OR_{15})(SR_{16})$, wherein $R_{17}$ and $R_{18}$, for each occurrence are, independently, H, an optionally substituted alkyl, an optionally substituted alkenyl, an optionally substituted alkynyl, an optionally substituted cyclyl, an optionally substituted heterocyclyl, an optionally substituted aryl, an optionally substituted heteroaryl, an optionally substituted aralkyl, or an optionally substituted heteralkyl; or $R_{17}$ and $R_{18}$ taken together with the nitrogen to which they are attached is optionally substituted heterocyclyl or optionally substituted heteroaryl; and $R_{15}$ and $R_{16}$ for each occurrence are, independently, H, an optionally substituted alkyl, an optionally substituted alkenyl, an optionally substituted alkynyl, an optionally substituted cyclyl, an optionally substituted heterocyclyl, an optionally substituted aryl, an optionally substituted heteroaryl, an optionally substituted aralkyl, or an optionally substituted heteralkyl. $R_{19}$, for each occurrence, is independently H, an optionally substituted alkyl, an optionally substituted cyclyl, an optionally substituted heterocyclyl, an optionally substituted aryl, an optionally substituted heteroaryl, an optionally substituted aralkyl, an optionally substituted heteroaralkyl, —$C(O)R^c$, —$OR_{15}$, —$SR_{15}$, —$NR_{17}R_{18}$, hydroxylalkyl, nitro, cyano, haloalkyl, aminoalkyl, or —$S(O)_2R^c$.

In addition, an alkyl, alkylene and any saturated portion of a alkenyl, cyclyl, alkynyl, aralkyl, heterocyclyl and heteroaralkyl groups, may also be substituted with =O, =S, =N—$R_{19}$.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

In one embodiment, suitable substituents for an alkyl, alkoxy, alkyl sulfanyl, alkylamino, dialkylamino, alkylene, alkenyl, alkynyl, cyclyl, heterocyclyl, aryl, aralkyl, and heteroaryl include, but are not limited to, halogen (F, Cl, Br, or I), hydroxyl, amino, alkylamino, arylamino, dialkylamino, diarylamino, cyano, nitro, mercapto, carbonyl, carbamido, carbamyl, carboxyl, thioureido, thiocyanato, sulfoamido, alkyl, alkenyl, alkyloxy, aryl, heteroaryl, cyclyl, heterocyclyl, wherein alkyl, alkenyl, alkyloxy, aryl, heteroaryl cyclyl, and heterocyclyl are optionally substituted with alkyl, aryl, heteroaryl, halogen, hydroxyl, mercapto, cyano, or nitro.

Choices and combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject). Typically, such compounds are stable at a temperature of 40° C. or less, in the absence of excessive moisture, for at least one week. Such choices and combinations will be apparent to those of ordinary skill in the art and may be determined without undue experimentation.

As used herein, the terms "animal", "subject" and "patient", include, but are not limited to, a cow, monkey, horse, sheep, pig, chicken, turkey, quail, cat, dog, mouse, rat, rabbit, guinea pig and human (preferably, a human).

As used herein, the term "lower" refers to a group having up to four atoms. For example, a "lower alkyl" refers to an alkyl radical having from 1 to 4 carbon atoms; a "lower alkenyl" or "lower alkynyl" refers to an alkenyl or alkynyl radical having from 2 to 4 carbon atoms, respectively; and a lower alkoxy refers to an alkoxy having 1 to 4 carbon atoms.

As used herein, the term "pharmaceutically acceptable solvate," is a solvate formed from the association of one or more solvent molecules to one of the compounds of formula (I), (II) or (III). The term solvate includes hydrates (e.g., mono-hydrate, dihydrate, trihydrate, tetrahydrate, and the like).

As used herein, the term "clathrate" means a compound of the present invention in the form of a crystal lattice that contains spaces (e.g., channels) that have a guest molecule (e.g., a solvent or water) trapped within.

As used herein, the term "pre-osteoclast cell" is a cell capable of forming an osteoclast cell upon differentiation and/or fusion and includes without limitation, circulating monocytes and tissue macrophages (N. Kurihara et al., Endocrinology 126:2733-41 (1990)). Without wishing to be bound by theory, pre-osteoclasts are converted to activated osteoclasts in a process thought to involve two factors produced by pre-osteoblasts, M-CSF and ODF. These factors activate certain genes that are needed for the conversion of a pre-osteoclast into an osteoclast.

The disalts described herein are useful to treat and prevent any IL-12 production-related disorders, e.g., inflammatory disorders, immune diseases, neurological disorders and bone loss diseases.

The term "inflammatory disorders" includes any inflammatory disease, disorder or condition caused, exasperated or mediated by IL-12 production. Such inflammatory disorders may include, without limitation, asthma, adult respiratory distress syndrome, systemic lupus erythematosus, inflammatory bowel disease (including Crohn's disease and ulcerative colitis), multiple sclerosis, insulin-dependent diabetes mellitus, autoimmune arthritis (including rheumatoid arthritis, juvenile rheumatoid arthritis, psoriatic arthritis), inflammatory pulmonary syndrome, pemphigus vulgaris, idiopathic thrombocytopenic purpura, autoimmune meningitis, myasthenia gravis, autoimmune thyroiditis, dermatitis (including atopic dermatitis and eczematous dermatitis), psoriasis, Sjogren's Syndrome (including keratoconjunctivitis sicca secondary to Sjogren's Syndrome), alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions (such as Stevens-Johnson syndrome), leprosy reversal reactions, erythema nodosum leprosum, autoimmune uveitis, allergic encephalomyelitis, aplastic anemia, pure red cell anemia, idiopathic thrombocytopenia, polychondritis, Wegener's granulomatosis, chronic active hepatitis, Graves ophthalmopathy, primary biliary cirrhosis, uveitis posterior and interstitial lung fibrosis.

"Inflammatory disorders" expressly include acute inflammatory disorders. Examples of acute inflammatory disorders include graft versus host disease, transplant rejection, septic shock, endotoxemia, Lyme arthritis, infectious meningitis (e.g., viral, bacterial, Lyme disease-associated), an acute episode of asthma and acute episodes of an autoimmune disease.

"Inflammatory disorders" expressly include chronic inflammatory disorders. Nonlimiting examples of chronic inflammatory disorder include asthma, rubella arthritis, and chronic autoimmune diseases, such as systemic lupus erythematosus, psoriasis, inflammatory bowel disease, including Crohn's disease and ulcerative colitis, multiple sclerosis and rheumatoid arthritis.

The term "immune diseases" includes any immune disease, disorder or condition caused, exasperated or mediated by IL-12 production. Such immune diseases may include, without limitation, rheumatoid arthritis, juvenile rheumatoid arthritis, systemic onset juvenile rheumatoid arthritis, psoriatic arthritis, ankylosing spondylitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary biliary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, Hashimoto's thyroiditis, osteoporosis, hypothalamic-pituitary-adrdrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to asthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The term "neurological disorder" includes any neurological disease, disorder or condition caused, exasperated or mediated by IL-12 production. Such neurological disorders may include, without limitation, neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, a-betalipoprotemia, ataxia, telangiectasia, and mitochondrial multi-system disorder); demyelinating core disorders, such as multiple sclerosis, acute transverse myelitis; and disorders of the motor unit such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16, Edition, Merck & Company, Rahway, N.J. (1992)

In the case of overlap in these definitions, the disease, condition or disorder may be considered to be a member of any of the above listed classes of IL-12 production-related disorders.

The term "disalt" refers to an ionic substances of formula A having a cationic, diprotonated IL-12 production inhibitor compound, $(\Delta)(2H^+)$, combined with anionic, charge balancing moieties, $n(\Sigma)$. In general, disalts can be formed by $$\{[(\Delta)(2H^+)]^{2+} \cdot [n(\Sigma)]^{2-}\} \qquad (A)$$

contacting IL-12 production inhibitor compounds $((\Delta)$ in formula A) with Bronsted acids. As used herein, the term "Bronsted acid" includes any chemical species that can be proton ($H^+$) donors. While not wishing to be bound by theory, it is believed that disalt formation occurs when two or more ($H^+$)-acceptor atoms, e.g., nitrogen atoms, of the IL-12 production inhibitor compounds are protonated by the Bronsted acid. Thus, in some embodiments, the charge balancing moieties ($n(\Sigma)$ in formula A) correspond to the conjugate base of the Bronsted acid used to protonate the IL-12 production inhibitor compounds. In other embodiments, disalt protons (($2H^+$) in formula A) and charge balancing moieties can be replaced in subsequent exchange reactions. For example, the disalt protons can be exchanged, e.g., for the corresponding isotopic deuterons ($2D^+$) or tritons ($2T^+$), and/or the disalt charge balancing moieties can be exchanged for other negatively charged counterions, e.g., via ion exchange chromatography methods. Disalts prepared via anion and/or cation exchange reactions of disalt starting materials are also within the scope of the present invention.

The disalts described herein can have a relatively high solubility, e.g., water solubility. As used herein, the "solubility" of a disalt in a solvent refers to the maximum mass of a disalt that can be dissolved per unit volume of the solvent under accelerated dissolution conditions (50-60° C. with concomitant ultrasonic agitation of the disalt/solvent test sample). Unless otherwise indicated, solubility data is expressed in terms of units of milligrams (mg)/milliliter (mL), e.g., mg/mL.

In some embodiments, the disalt solubility in water can be at least about 10 mg/mL (e.g., at least about 15 mg/mL, at least about 25 mg/mL, at least about 50 mg/mL, at least about 60 mg/mL, at least about 70 mg/mL, at least about 80 mg/mL, at least about 90 mg/mL, at least about 100 mg/mL, at least about 150 mg/mL, at least about 200 mg/mL, at least about 225 mg/mL, at least about 250 mg/mL, at least about 275 mg/mL, at least about 300 mg/mL, at least about 350 mg/mL, at least about 400 mg/mL, at least about 450 mg/mL, at least about 500 mg/mL, at least about 550 mg/mL, at least about 600 mg/mL, at least about 650 mg/mL, at least about 700 mg/mL, at least about 750 mg/mL, at least about 800 mg/mL, at least about 850 mg/mL, at least about 900 mg/mL, at least about 950 mg/mL, at least about 1,000 mg/mL).

The inventors have discovered that there can be unexpected differences in solubility between a disalt and a monosalt. As used herein, the term "monosalt" refers to ionic substances having a cationic, monoprotonated IL-12 production inhibitor compound, e.g., $(\Delta)(1H^+)$, combined with an anionic, charge balancing moiety, e.g., $[1(\Sigma)]^{-1}$. For example, the inventors have discovered that the solubility of a disalt can be unexpectedly higher (i.e., more positive and greater in magnitude) than the solubility of the corresponding monosalt (i.e., the solubility of $\{[(\Delta)(2H^+)]^{2+}\cdot[n(\Sigma)]^{2-}\}$ can be unexpectedly higher than the solubility of $\{[(\Delta)(1H^+)]^{1+}\cdot[n(\Sigma)]^{1-}\}$). Further, in some instances, the solubility of disalt can be unexpectedly higher than monosalts differing in the identity of either ($\Delta$) and/or ($\Sigma$) (i.e., the solubility of $\{[(\Delta)(2H^+)]^{2+}\cdot[n(\Sigma)]^{2-}\}$ can be unexpectedly higher than the solubility of $\{[(\Delta')(1H^+)]^{1+}\cdot[n(\Sigma)]^{1-}\}$). In some embodiments, the solubility of disalts can be about 2 times higher (e.g., about 3 times higher, about 4 times higher, about 5 times higher, about 6 times higher, about 7 times higher, about 8 times higher, about 9 times higher, about 10 times higher, about 11 times higher, about 12 times higher, about 13 times higher, about 14 times higher, about 15 times higher, about 16 times higher, about 17 times higher, about 18 times higher, about 19 times higher, or about 20 times higher) than the solubility of monosalts.

Thus, disalts can have one or more advantages over monosalts as active ingredients in pharmaceutical formulations and compositions for treatment of IL-12 related diseases or disorders, e.g., those IL-12 related diseases or disorders described herein. While not wishing to be bound by theory, it is believed that, e.g., the higher solubility of the disalts relative to the monosalts can render a disalt pharmaceutical formulation or composition more bioavailable than a monosalt pharmaceutical formulation or composition. Again, while not wishing to be bound by theory, it is believed that, e.g., the higher solubility of the disalts relative to the monosalts would increase the likelihood that liquid-based disalt compositions and formulations could be prepared at higher concentrations than liquid-based monosalt compositions and formulations, thereby advantageously minimizing the volume of liquid carrier needed to prepare the formulation or composition. It is also believed that, e.g., the higher solubility of the disalts relative to the monosalts would increase the likelihood that disalts could be solubilized more quickly than monosalts, thereby advantageously minimizing composition/formulation preparation times.

The IL-12 production inhibitor compounds used to form disalts (i.e., $\Delta$ in formula A) can include compounds having any one of formulas Ia, IIa, and IIIa below (definitions for each of the variables in formulas Ia, IIa, and IIIa are as provided above).

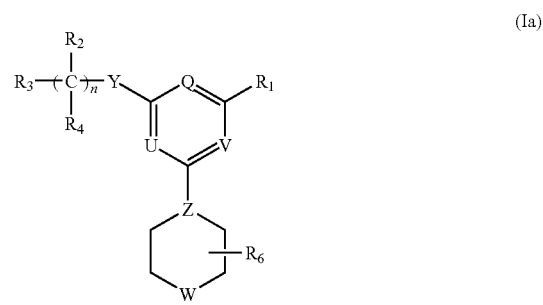

(Ia)

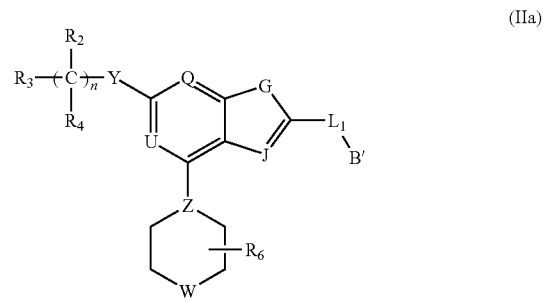

(IIa)

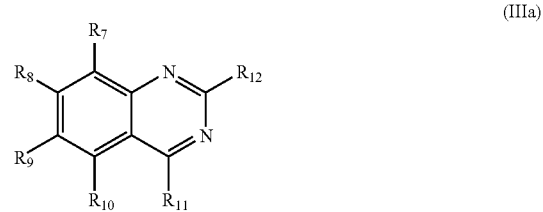

(IIIa)

Examples of such IL-12 production inhibitor compounds are provided below:

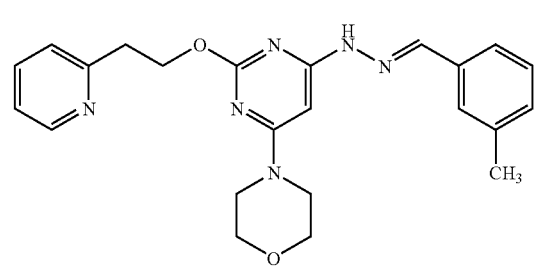

1

2
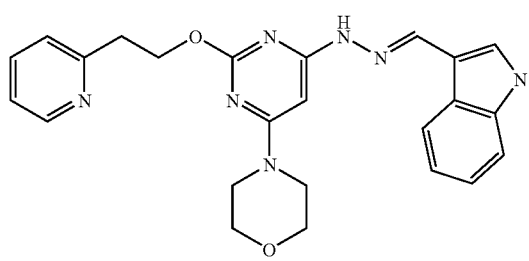
7
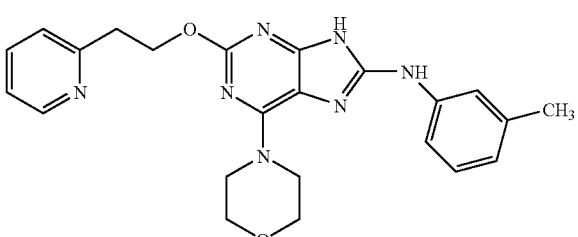
3
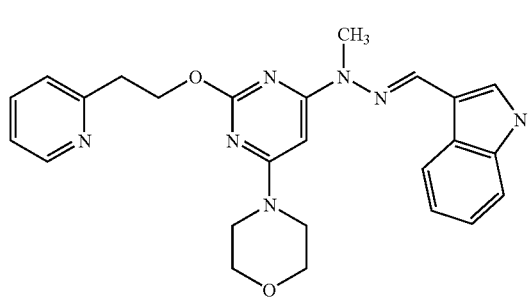
8
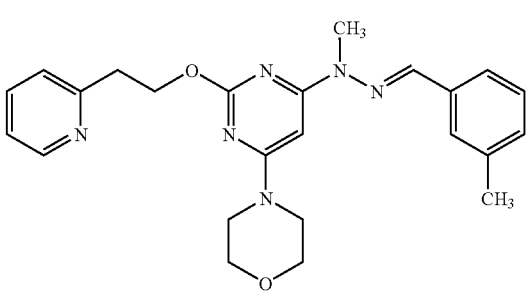
4
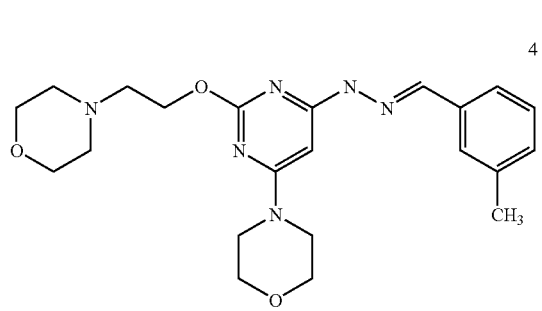
9
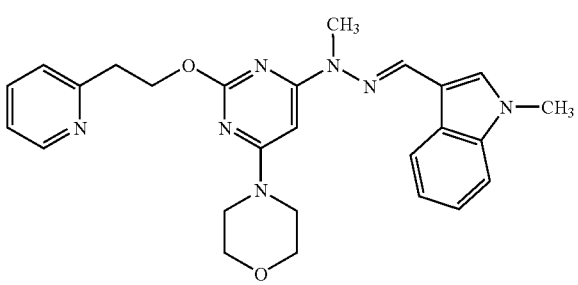
5
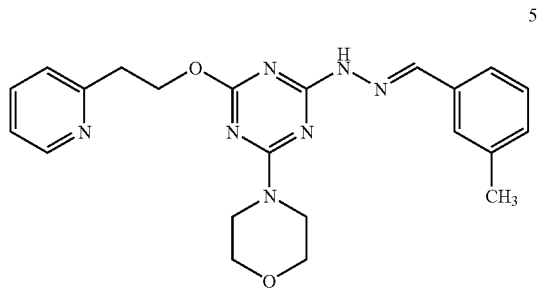
10
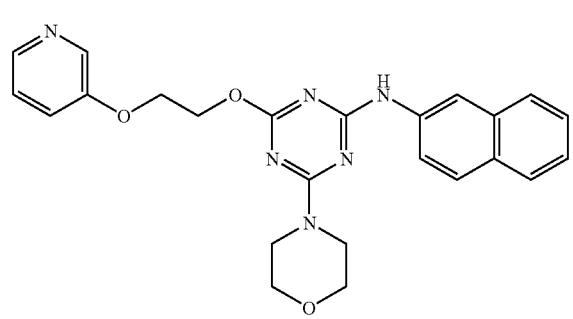
6
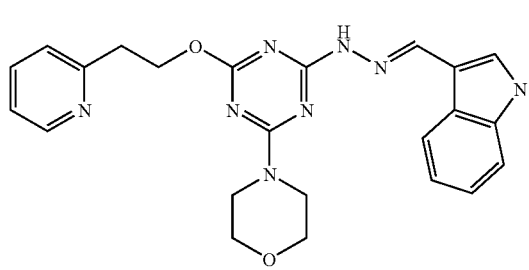
11
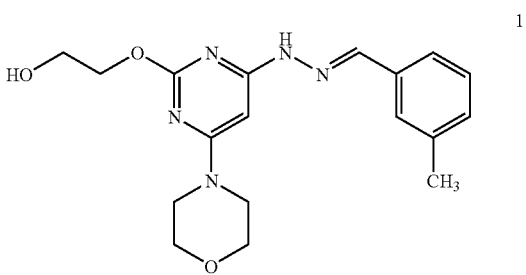

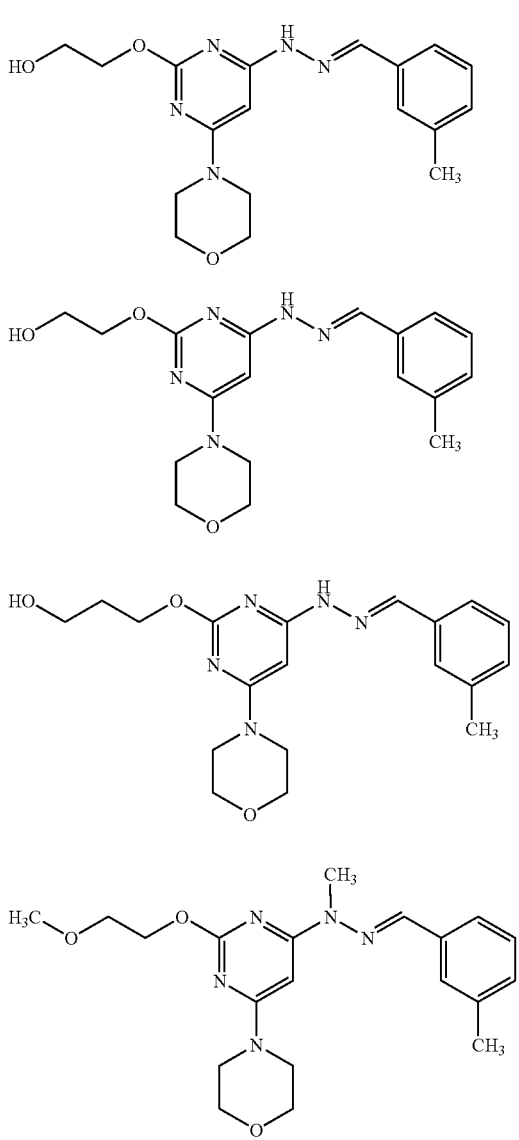

The synthesis and IL-12 production inhibitory activities of compounds having formulas Ia, IIa, and IIIa, e.g., compounds 1-14, as well as other useful IL-12 production inhibitor compounds, are described in, e.g., Ono, et al., U.S. Pat. No. 6,384,032, entitled "Inhibitors of IL-12 Production;" Ono, et al., U.S. Pat. No. 6,680,315, entitled "Triazine Compounds;" Ono, et al., U.S. Pat. No. 6,693,097, entitled "Pyrimidine Compounds;" Sun, et al., U.S. Pat. No. 6,660,733, entitled "Pyrimidine Compounds;" U.S. patent application Ser. No. 10/686,505, filed on Oct. 14, 2003, entitled "Novel Compounds;" U.S. Pat. No. 6,858,606, filed on Nov. 26, 2002, entitled "Pyrimidine Compounds;" U.S. patent application Ser. No. 10/985,696, filed on Nov. 10, 2004, and entitled "Pyridine Compounds;" U.S. patent application Ser. No. 10/985,716, filed on Nov. 10, 2004, and entitled "Heteroaryl Hydrazone Compounds;" U.S. patent application Ser. No. 10/985,627, filed on Nov. 10, 2004, and entitled "Quinazoline Compounds;" and U.S. Provisional Patent Application Ser. No. 60/626,609, filed Nov. 10, 2004, and entitled "Process for Trisubstituted Pyrimidine Compounds." The entire teachings of the above mentioned patents and patent applications are incorporated herein by reference.

In some embodiments, disalt formation can occur when two or more of the (H$^+$)-acceptor atoms on the IL-12 production inhibitor compounds are nitrogen atoms.

In some embodiments, it can be desirable to have $R_3$ in formulas Ia and Ia be an amino group; an alkylamino group; a dialkylamino group; a heterocyclyl group having at least one basic nitrogen atom, e.g., a heterocyclyl group having an alkyl or unsubstituted ring nitrogen atom, such as a morpholino group; or a heteroaryl group having at least one basic nitrogen atom, e.g., a heteroaryl group having a nitrogen atom in which the lone pair does not form part of the aromatic π-electron system, such as a pyridinyl group.

In some embodiments, it can be desirable to have hydrazone linkages, e.g., —N($R^c$)—N=C—, and/or amino linkages, —N($R^c$)—, form part of the substituents $R_1$, $L_1$-B', or $R_{12}$ in formulas Ia, IIa, and IIIa, respectively. $R^c$ can be, independently, hydrogen or lower alkyl, e.g., $CH_3$, in either of the above linkages.

In some embodiments, it can be desirable to have Z be nitrogen and W be oxygen in formulas Ia and IIa and to have one of $R_{11}$ or $R_{12}$ in formula IIIa be a morpholino group.

In some embodiments, it can be desirable to have $R_3$ in formulas Ia and IIa be an amino group; an alkylamino group; a dialkylamino group; a heterocyclyl group having at least one basic nitrogen atom as described above; or a heteroaryl group having at least one basic nitrogen atom as described above; and to have either hydrazone linkages, e.g., —N($R^c$)—N=C—, and/or amino linkages, —N($R^c$)—, form part of the substituents $R_1$ or $L_1$-B' in formulas Ia and IIa, respectively.

In general, Bronsted acids useful for forming the disalts described herein can have a pKa (relative to water) in the range of between about −15 and about +5 (e.g., about −15 to about −14, about −15 to about −13, about −15 to about −12, about −15 to about −11, about −15 to about −10, about −15 to about −9, about −15 to about −8, about −15 to about −7, about −15 to about −6, about −15 to about −5, about −15 to about −4, about −15 to about −3, about −15 to about −2, about −15 to about −1, about −15 to about 0, about −15 to about 0.7, about −15 to about 1, about −15 to about 2, about −15 to about 3, about −15 to about 4). For example, see P. Heinrich Stahl, Camille G. Wermuth. *Handbook of Pharmaceutical Salts*. Wiley-Vch. (2002) p.145-149. Exemplary acids include without limitation, hydrochloric (HCl); nitric ($HNO_3$); sulfuric ($H_2SO_4$); hydrobromic (HBr); hydroiodic (HI); perchloric ($HClO_4$); phosphoric acid ($H_3PO_4$); alkylsulfonic acids, e.g., methanesulfonic ($CH_3SO_3H$), and halogenated analogs thereof, e.g., trifluoromethanesulfonic ($CF_3SO_3H$); arylsulfonic acids, e.g., benzenesulfonic ($C_6H_5SO_3H$) or p-toluenesulfonic acid p-Tol$SO_3H$); halogenated acetic acids, e.g., trifluoroacetic ($CF_3CO_2H$), trichloroacetic ($CCl_3CO_2H$), dichloroacetic ($CHCl_2CO_2H$), fluoroacetic ($FCH_2CO_2H$), and chloroacetic ($ClCH_2CO_2H$)); picric (($O_2N$)$_3C_6H_2OH$); oxalic (($CO_2H$)$_2$); citric (C(OH)($CH_2CO_2H$)$_2CO_2H$); formic ($HCO_2H$); ascorbic acid; and benzoic acid ($C_6H_5CO_2H$) and derivatives thereof. In some embodiments, it can be desirable to use alkylsulfonic acids, e.g., methanesulfonic ($CH_3SO_3H$). Other useful acids (and pKa values) are described in P. Heinrich Stahl, Camille G. Wermuth. *Handbook of Pharmaceutical Salts*. Wiley-Vch. (2002) p.145-149.

In some embodiments, IL-12 production inhibitor compounds can be contacted with at least two equivalents of a monoprotic Bronsted acid, e.g., HM; a diprotic Bronsted acid, e.g., $H_2M$; or a polyprotic Bronsted acid; e.g., $H_3M$, to provide disalts having formulas,

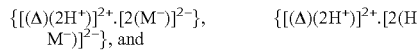

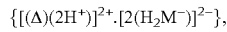

respectively. In some embodiments, IL-12 production inhibitor compounds can be contacted with at least one equivalent of a diprotic Bronsted acid, a polyprotic acid Bronsted, or a bifunctional Bronsted acid, e.g., HM—MH, to provide disalts having formulas,

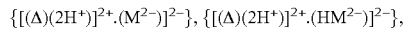

and

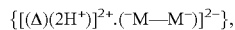

respectively.

In some embodiments, disalts can be prepared by contacting an IL-12 production inhibitor compound with a solvent to form a solution or suspension and contacting the solution or suspension with a Bronsted acid. In certain embodiments, the solution or suspension contains at most about 1 weight percent of the IL-12 production inhibitor compound (e.g., at most about 2 weight percent of the IL-12 production inhibitor compound, at most about 5 weight percent of the IL-12 production inhibitor compound, at most about 10 weight percent of the IL-12 production inhibitor compound, at most about 15 weight percent of the IL-12 production inhibitor compound, at most about 20 weight percent of the IL-12 production inhibitor compound, at most about 30 weight percent of the IL-12 production inhibitor compound, at most about 40 weight percent of the IL-12 production inhibitor compound, or at most about 50 weight percent of the IL-12 production inhibitor compound). In some embodiments, the IL-12 production inhibitor compound and the solvent can be combined at room temperature, e.g., 25° C., to form a suspension, and the suspension can be heated to at most about 60° C. (at most about 70° C. or at most about 80° C.) to form a solution. In other embodiments, the Bronsted acid can be added to the suspension at room temperature to form a solution. In some embodiments, it can be desirable to form the IL-12 production inhibitor compound solution, e.g., by heating, prior to adding the Bronsted acid. The Bronsted acid can be added neat, e.g., as a solid, liquid, or gas, or as a solution, e.g., HCl in ether. In some embodiments, it can be desirable to add an amount of the Bronsted acid that is in excess of the stoichiometric amount of acid that is calculated to be needed for disalt formation.

In some embodiments, the solvent can be a $C_1$-$C_4$ alcohol, e.g., ethanol (e.g., absolute ethanol), isopropanol, or 2,2,2-trifluoroethanol. In certain embodiments, the solvent can be a mixed solvent system comprising two or more solvents and can be a homogeneous or heterogeneous solvent system. The constituent solvents of the mixed solvent system may be present either in equal or unequal amounts, e.g., 25:75, 50:50, 90:10. Examples of mixed solvent systems include absolute ethanol/toluene and absolute ethanol/chloroform.

Disalts can be isolated, e.g., by filtration of a precipitated disalt or by evaporation of a solution containing the formed disalt. Removal of bulk and/or residual solvents can be carried out, e.g., using one or more of the following techniques. In some embodiments, solvent removal can be carried out by natural evaporation (e.g., under ambient conditions with substantially no deliberate displacement of solvent vapors from the vicinity of the disalt or forced evaporation). In some embodiments, solvent removal can be carried out by deliberate displacement of solvent vapors from the vicinity of the disalt (e.g., by a directed stream of air or an inert gas, such as nitrogen or argon). Solvent removal can be carried out in vacuo, for example, at a pressure of at least about 0.05 mm Hg (e.g., at least about 0.1 mm Hg, at least about 0.50 mm Hg, at least about 1 mm Hg, at least about 5 mm Hg, at least about 10 mm Hg, at least about 30 mm Hg). In general, solvent removal can be optionally carried out, for example, at a temperature of at most about 70° C. (e.g., at most about 60° C., at most about 50° C., at most about 40° C., at most about 30° C., at most about 25° C.).

The extent of solvent removal can be monitored by gravimetric methods (e.g. drying of the disalt until a constant weight of the disalt is achieved) or spectroscopic techniques (e.g., removing a sample of the disalt and obtaining a $^1H$ NMR spectrum of the sample to detect the solvent).

In some embodiments, it can be desirable for the disalt to be substantially free of solvents.

In some embodiments, it can be desirable to isolate, formulate, and/or administer disalts that further include one or more solvents, e.g., as a result of solvate formation or occlusion of solvent molecules into the crystal lattice of the disalts. Disalts can have at most about 0.05 weight percent (e.g., at most about 0.1 weight percent, at most about 0.5 weight percent solvent, at most about 1 weight percent, at most about 2 weight percent, at most about 3 weight percent, at most about 4 weight percent, at most about 5 weight percent, at most about 10 weight percent, at most about 15 weight percent) of one or more solvents.

Both solvent-associated and substantially solvent-free disalts are within the scope of this invention.

In some instances, a disalt prepared by the methods described herein may further include the corresponding monosalt. In some embodiments, it can be desirable for the disalt to be substantially free of the monosalt. Monosalts can be removed, e.g., by recrystallization.

In some embodiments, it can be desirable to isolate, formulate, and/or administer disalts that further include the corresponding monosalt. Disalts can have at most about 0.05 weight percent (e.g., at most about 0.1 weight percent, at most about 0.5 weight percent solvent, at most about 1 weight percent, at most about 2 weight percent, at most about 3 weight percent, at most about 4 weight percent, at most about 5 weight percent, at most about 10 weight percent, at most about 15 weight percent, at most about 20 weight percent, at most about 25 weight percent, at most about 30 weight percent, at most about 35 weight percent, at most about 40 weight percent, at most about 45 weight percent,) of the monosalt.

Both monosalt-associated and substantially monosalt-free disalts are within the scope of this invention.

Also within the scope of this invention is a pharmaceutical composition that contains an effective amount of one or more of the disalts of this invention and a pharmaceutically acceptable carrier. Further, the present invention covers a method of administering an effective amount of such a disalt to a subject in need of treatment of IL-12 production related diseases (e.g., rheumatoid arthritis, sepsis, Crohn's disease, multiple sclerosis, psoriasis, or insulin-dependent diabetes mellitus). "An effective amount" refers to the amount of the disalt which is required to confer a therapeutic effect on the treated subject. The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the disalt of this invention can range from about 0.001 mg/Kg to about 1000 mg/Kg. Effective doses will also vary, as recognized by those skilled in the art, depending on the diseases treated, route of administration, excipient usage, and the possibility of co-usage with other therapeutic treatments such as use of other agents.

To practice the method of the present invention, a disalt, as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrastemal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A disalt of this invention can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the disalts of this invention, or one or more solubilizing agents, can be utilized as pharmaceutical excipients for delivery of the pyridine compounds. Examples of other carriers include colloidal silicon dioxide, magnesium stearate, cellulose, sodium lauryl sulfate, and D&C Yellow # 10.

In certain embodiments, pharmaceutical compositions and dosage forms of the invention comprise one or more active ingredients in relative amounts and formulated in such a way that a given pharmaceutical composition or dosage form inhibits the uptake of calcium. Preferred pharmaceutical compositions and dosage forms comprise a disalt described herein, or a pharmaceutically acceptable prodrug, solvate, or clathrate thereof, optionally in combination with one or more additional active agents.

The methods for treating or preventing disorders associated with excessive bone loss in a patient in need thereof can further comprise administering to the patient being administered a compound of this invention, an effective amount of one or more other therapeutic agents. Such therapeutic agents may include other therapeutic agents such as those conventionally used to prevent or treat disorders associated with excessive bone resorption or symptoms thereof. For example, such other agents include anti-resorptive agents for example progestins, polyphosphonates, bisphosphonate(s), estrogen agonists/antagonists, estrogen (such as Premarin®), estrogen/progestin combinations, and estrogen derivatives (such as estrone, estriol or 17α, 17β-ethynyl estradiol).

In such combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment of the invention where another therapeutic agent is administered to an animal, the effective amount of the compound of this invention is less than its effective amount would be where the other therapeutic agent is not administered. In another embodiment, the effective amount of the conventional agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, dthynodiol diacetate, etonogestrel, flurogestone acetate, gestaclone, gestodene, gestonorone caproate, gestrinone, haloprogesterone, hydroxyprogesterone, caproate, levonorgestrel, lynestrenol, medrogesterone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol. Preferred progestins are medroxyprogestrone, norethindrone and norethynodrel.

Exemplary bone resorption inhibiting polyphosphonates include polyphosphonates of the type disclosed in U.S. Pat. No. 3,683,080. Preferred polyphosphonates are geminal dipolyphosphonates (also referred to as bis-phosphonates). Tiludronate disodium is an especially preferred polyphosphonate. Ibandronic acid is an especially preferred polyphosphonate. Alendronate is an especially preferred polyphosphonate. Zoledronic acid is an especially preferred polyphosphonate. Other preferred polyphosphonates are 6-amino-1-hydroxy-hexylidene-bisphosphonic acid and 1-hydroxy-3-(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy-1,1-diphosphonic acid, methane diphosphonic acid, pentane-1-hydroxy- 1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl)amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the disalts of this invention may be combined with a mammalian estrogen agonist/antagonist. Any estrogen agonist/antagonist may be used for this purpose. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue; and blocking the actions of estrogen in one or more tissues. Such activities are readily determined by those skilled in the art of standard assays including estrogen receptor binding assays, standard bone histomorphometric and densitometer methods, and E. F Eriksen et al., Bone Histomorphometry, Raven Press, New York, pp. 1-74 (1994); S. J. Grier et. al., The Use of Dual-Energy X-Ray Absorptiometry In Animals, Inv. Radiol. 31(1):50-62 (1996); Walher H. W. and Fogelman I., The Evaluation of Osteoporosis: Dual Energy X-Ray Absorptiometry in Clinical Practice., Martin Dunitz Ltd., London, pp. 1-296 (1994)). A variety of these compounds are described and referenced below.

A preferred estrogen agonist/antagonist is droloxifene: (phenol, 3-(1-(4-(2-(dimethylamino)ethoxy)phenyl)-2-phenyl-1-butenyl)-, (E)-) and related compounds which are disclosed in U.S. Pat. No. 5,047,431. Another preferred estrogen agonist/antagonist is 3-(4-(1,2-diphenyl-but-1-enyl)-phenyl)-acrylic acid, which is disclosed in Wilson et al., Endocrinology 138:3901-11 (1997). Another preferred estrogen agonist/antagonist is tamoxifen: (ethanamine,2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516. Another related compound is 4-hydroxy tamoxifen which is disclosed in U.S. Pat. No. 4,623,660.

A preferred estrogen agonist/antagonist is raloxifene: (methanone, (6-hydroxy-2-(4-hydroxyphenyl)benzo[b] thien-3-yl)(4-(2-(1-piperidinyl)ethoxy)phenyl)hydrochloride) which is disclosed in U.S. Pat. No. 4,418,068. Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225. Another preferred estrogen agonist/antagonist is centchroman: 1-(2-((4-(-methoxy-2,2,dimethyl-3-phenyl-chroman-4-yl)-phenoxy)-ethyl)-pyrrolidine, which is disclosed in U.S. Pat. No. 3,822,287. Also preferred is levormeloxifene. Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155. Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058. Another preferred estrogen agonist/antagonist is 6-(4-hydroxy-phenyl)-5-(4-(2-piperidin-1-yl-ethoxy)-benzyl)-naphthalen-2-ol which is disclosed in U.S. Pat. No. 5,484,795. Another preferred estrogen agonist/antagonist is (4-(2-(2-aza-bicyclo[2.2.1]hept-2-yl)-ethoxy)-phenyl)-(6-hydroxy-2-(4-hydroxy-phenyl)-benzo[b]thiop hen-3-yl)-methanone which is disclosed, along with methods of preparation, in PCT publication no. WO 95/10513 assigned to Pfizer Inc. Other preferred estrogen agonist/antagonists include compounds as described in U.S. Pat. No. 5,552,412. Especially preferred compounds described therein are: cis-6-(4-fluoro-phenyl)-5-(4-(2-piperidin-1-yl-ethoxy)-phenyl)-5,6,7,8-tetrahydronaphthalen-2-ol; (-)-cis-6-phenyl-5-(4-(2-pyrrolidin-1-yl-ethoxy)-phenyl)-5,6,7,8-tetrahydronaphthalen-2-ol; cis-6-phenyl-5-(4-(2-pyrrolidin-1-yl-ethoxy)-phenyl)-5,6,7,8-tetrahydro-naphthalen-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-(4-(2-piperidin-1-yl-ethoxy)-phenyl)-5,6,7,8-tetrahydro-naphthalen-2-ol; and 1-(4'-pyrrolidinolethoxyphenyl)-2-phenyl-6-hydroxy-1,2,3,4-tetrahydroisoquinoline. Other estrogen agonist/antagonists are described in U.S. Pat. No. 4,133,814. U.S. Pat. No. 4,133,814 discloses derivatives of 2-phenyl-3-aroyl-benzothiophene and 2-phenyl-3-aroylbenzothiophene-1-oxide.

Those skilled in the art will recognize that other bone anabolic agents, also referred to as bone mass augmenting agents, may be used in conjunction with the compounds of this invention. A bone mass augmenting agent is a compound that augments bone mass to a level which is above the bone fracture threshold as detailed in the World Health Organization Study World Health Organization, "Assessment of Fracture Risk and its Application to Screening for Postmenopausal Osteoporosis (1994). Report of a WHO Study Group. World Health Organization Technical Series 843." Any prostaglandin, or prostaglandin agonist/antagonist may be used in combination with the compounds of this invention. Those skilled in the art will recognize that IGF-1, sodium fluoride, parathyroid hormone (PTH), active fragments of parathyroid hormone, growth hormone or growth hormone secretagogues may also be used. The following paragraphs describes in greater detail exemplary compounds that may be administered in combination with compounds of this invention Prostaglandins: The term prostaglandin refers to compounds which are analogs of the natural prostaglandins $PGD_1$, $PGD_2$, $PGE_2$, $PGE_1$, and $PGF_2$ which are useful in the treatment of osteoporosis and other disorders associated with excessive osteoclastic bone resorption. These compounds bind to the prostaglandins receptors. Such binding is readily determined by those skilled in the art of standard assays (e.g., S. An et al., Cloning and Expression of the $EP_2$ Subtype of Human Receptors for Prostaglandin $E_2$ Biochemical and Biophysical Research Communications, 197(1): 263-270 (1993)).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while $PGE_2$ contains a trans unsaturated double bond at the $C_{13}$-$C_{14}$ and a cis double bond at the $C_5$-$C_6$ position.

A variety of prostaglandins are described and referenced below. However, other prostaglandins will be known to those skilled in the art. Exemplary prostaglandins are disclosed in U.S. Pat. Nos. 4,171,331 and 3,927,197,. Norrdin et al., The Role of Prostaglandins in Bone in Vivo, Prostaglandins Leukotriene Essential Fatty Acids 41: 139-150 (1990) is a review of bone anabolic prostaglandins. Any prostaglandin agonist/antagonist may be used in combination with the compounds of this invention. The term prostaglandin agonist/antagonist refers to compounds which bind to prostaglandin receptors (e.g., An S. et al., Cloning and Expression of the $EP_2$ Subtype of Human Receptors for Prostaglandin $E_2$, Biochemical and Biophysical Research Communications 197(1):263-70 (1993)) and mimic the action of prostaglandin in vivo (e.g., stimulate bone formation and increase bone mass). Such actions are readily determined by those skilled in the art of standard assays. Eriksen E. F. et al., Bone Histomorphometry, Raven Press, New York, 1994, pp. 1-74; S. J. Grier et al., The Use of Dual-Energy X-Ray Absorptiometry In Animals, Inv. Radiol. 31(1):50-62 (1996); H. W. Wahner and I. Fogelman, The Evaluation of Osteoporosis: Dual Energy X-Ray Absorptiometry in Clinical Practice, Martin Dunitz Ltd. London, pp. 1-296 (1994). A number of these compounds are described and reference below. However, other prostaglandin agonists/antagonists will be known to those skilled in the art. Exemplary prostaglandin agonists/antagonists are disclosed as follows. U.S. Pat. No. 3,932,389 discloses 2-descarboxy-2-(tetrazol-5-yl)-11-desoxy-15-substituted-omega-pentanorprostaglandins useful for bone formation activity. U.S. Pat. No. 4,018,892, discloses 16-aryl-13,14-dihydro-$PGE_2$ p-biphenyl esters useful for bone formation activity. U.S. Pat. No. 4,219,483, discloses 2,3,6-substituted-4-pyrones useful for bone formation activity. U.S. Pat. No. 4,132,847, discloses 2,3,6-substituted-4-pyrones useful for bone formation activity. U.S. Pat. No. 4,000,309, discloses 16-aryl-13,14-dihydro-$PGE_2$ p-biphenyl esters useful for bone formation activity. U.S. Pat. No. 3,982,016, discloses 16-aryl-13,14-dihydro-$PGE_2$ p-biphenyl esters useful for bone formation activity. U.S. Pat. No. 4,621,100, discloses substituted cyclopentanes useful for bone formation activity. U.S. Pat. No. 5,216,183, discloses cyclopentanones useful for bone formation activity.

Sodium fluoride may be used in combination with the compounds of this invention. The term sodium fluoride refers to sodium fluoride in all its forms (e.g., slow release sodium fluoride, sustained release sodium fluoride). Sustained release sodium fluoride is disclosed in U.S. Pat. No. 4,904,478. The activity of sodium fluoride is readily determined by those skilled in the art of biological protocols.

Bone morphogenetic protein may be used in combination with the disalts of this invention (e.g., see Ono et al., Promotion of the Osteogenetic Activity of Recombinant Human Bone Morphogenetic Protein by Prostaglandin $E_1$, Bone 19(6):581-588 (1996)).

Any parathyroid hormone (PTH) may be used in combination with the compound of this invention. The term parathyroid hormone refers to parathyroid hormone, fragments or metabolites thereof and structural analogs thereof which can stimulate bone formation and increase bone mass. Also included are parathyroid hormone related peptides and active fragments and analogs of parathyroid related peptides (see PCT publication No. WO 94/01460). Such bone anabolic functional activity is readily determined by those skilled in the art of standard assays. A variety of these compounds are described and referenced below. However, other parathyroid hormone will be known to those skilled in the art. Exemplary parathyroid hormones are disclosed in the following references. "Human Parathyroid Peptide Treatment of Vertebral Osteoporosis", Osteoporosis Int., 3, (Supp 1):199-203. "PTH 1-34 Treatment of Osteoporosis with Added Hormone Replacement Therapy: Biochemical, Kinetic and Histological Responses" Osteoporosis Int. 1: 162-170.

Any growth hormone or growth hormone secretagogue may be used in combination with the compounds of this invention. The term growth hormone secretagogue refers to a compound which stimulates the release of growth hormone or mimics the action of growth hormone (e.g., increases bone formation leading to increased bone mass). Such actions are readily determined by those skilled in the art of standard assays well known to those of skill in the art. A variety of these compounds are disclosed in the following published PCT patent applications: WO 95/14666; WO 95/13069; WO 94/19367; WO 94/13696; and WO 95/34311. However, other growth hormones or growth hormone secretagogues will be known to those skilled in the art. In particular, a preferred growth hormone secretagogue is N-[1(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide:MK-667. Other preferred growth hormone secretagogues include 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide or its L-tartaric acid salt; 2-amino-N-(1-(R)-benzyloxymethyl-2-(3a-(R)-(4-fluoro-benzyl)-2-methyl-3-oxo -2,3,3a,4, 6,7-hexahydro-pyrazolo[4,3-c]pyridin-5-yl)-2-oxo-ethyl) isobutyramide; 2-amino-N-(2-(3a-(R)-benzyl-3-oxo-2,2,3a, 4,6,7-hexahydro-pyrazolo[4,3-c]pyridin-5-yl)-1-(R) benzyloxymethyl-2-oxo-ethyl)isobutyramide; and 2-amino-N-(1-(2,4-difluoro-benzyloxymethyl)-2-oxo-2-(3-oxo-3a-pyridin-2-ylm ethyl-2-(2,2,2-trifluoro-ethyl)-2,3,3a,4,6,7-hexahydro-pyrazolo[4,3-c]pyridin-5-yl)-ethyl)-2-methyl-propionamide.

The other therapeutic agent can be a steroid or a non-steroidal anti-inflammatory agent. Useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicarn, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see Paul A. Insel, Analgesic-Antipyretic and Antiinflammatory Agents and Drugs Employed in the Treatment of Gout, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

For arthritis, inflammation-mediated bone loss and other disorders that have an inflammatory component, preferred conventional treatments for use in combination therapy with the compounds and compositions of this invention include (without limitation) naproxen sodium (Anaprox® and Anaprox® DS, Roche), flurbiprofen (Ansaid®; Pharmacia), diclofenac sodium+misoprostil (Arthrotec®, Searle), valdecoxib (Bextra®, Pharmacia), diclofenac potassium (Cataflam® and Voltaren®, Novartis), celecoxib (Celebrex®, Pfizer), sulindac (Clinoril®, Merck), oxaprozin (Daypro®, Pharmacia), salsalate (Disalcid®, 3M), diflunisal (Dolobid®, Merck), naproxen sodium (EC Naprosyn®, Roche), piroxicam (Feldene®, Pfizer), indomethacin (Indocin® and Indocin SR®, Merck), etodolac (Lodine® and Lodine XL®, Wyeth), meloxicam (Mobic®, Boehringer Ingelheim), ibuprofen (Motrin®, Pharmacia), naproxen (Naprelan®, Elan), naproxen (Naprosyn®, Roche), ketoprofen (Orudis® and Oruvail®, Wyeth), nabumetone (Relafen®, SmithKline), tolmetin sodium (Tolectin®, McNeil), choline magnesium trisalicylate (Trilisate®, Purdue Fredrick), and rofecoxib (Vioxx®, Merck).

In any case where pain in a component of the target disorder, the other therapeutic agent can be an analgesic. Useful analgesics include, but are not limited to, phenacetin, butacetin, acetaminophen, nefopam, acetoamidoquinone, and mixtures thereof.

For use against osteoporosis, Paget's disease and other disorders associated with bone deterioration, preferred conventional agents that may be used in combination with compounds and compositions of this invention include (without limitation) bisphosphonates (such as etidronate (Didronel®, Procter & Gamble), pamidronate (Aredia®, Novartis), and alendronate (Fosamax®, Merck)), tiludronate (Skelid®, Sanofi-Synthelabo, Inc.), risedronate (Actonel®, Procter & Gamble/Aventis), calcitonin (Miacalcin®), estrogens (Climara®, Estrace®, Estraderm®, Estratab®, Ogen®, Ortho-Est®, Vivelle®, Premarin®, and others) estrogens and progestins (Activella™, FemHrt®, Premphase®, Prempro®, and others), parathyroid hormone and portions thereof, such as teriparatide (Forteo®, Eli Lilly and Co.), selective estrogen receptor modulators (SERMs) (such as raloxifene (Evista®)) and treatments currently under investigation (such as other parathyroid hormones, sodium fluoride, vitamin D metabolites, and other bisphosphonates and selective estrogen receptor modulators).

Any method of the present invention can comprise administering an effective amount of a composition or pharmaceutical composition comprising at least one disalt of this invention to a cell, tissue, organ, animal or patient in need of such modulation, treatment or therapy. Such a method can optionally further comprise co-administration or combination therapy for treating an IL-12 production related disorder, wherein the administering further comprises administering before, concurrently with, and/or after the compound of this invention, at least one additional active agent selected from a TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteroid, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

TNF antagonists suitable for compositions, combination therapy, co-administration, devices and/or methods of the present invention include, but are not limited to, anti-TNF antibodies (such as, Remicade (Infliximab) or Humira (adalimumab)) for example, or, antigen-binding fragments thereof, and receptor molecules which bind specifically to TNF (such as, for example, Enbrel (Etanercept)); compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

For clarification, a "tumor necrosis factor antibody," "TNF antibody," "TNF antibody," or fragment and the like decreases, blocks, inhibits, abrogates or interferes with TNF activity in vitro, in situ and/or preferably in vivo. For example, a suitable TNF human antibody of the present invention can bind TNF-α and includes anti-TNF antibodies, antigen-binding fragments thereof, and specified mutants or domains thereof that bind specifically to TNFa. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

The foregoing and other useful combination therapies will be understood and appreciated by those of skill in the art.

Potential advantages of such combination therapies include the ability to use less of each of the individual active ingredients to minimize toxic side effects, synergistic improvements in efficacy, improved ease of administration or use and/or reduced overall expense of compound preparation or formulation.

The biological activities of a disalt can be evaluated by a number of cell-based assays. One of such assays can be conducted using cells from human peripheral blood mononuclear cells (PBMC) or human monocytic cell line (THP-1). The cells are stimulated with a combination of human interferon-γ (IFNγ) and lipopolysaccharide or a combination of IFNγ and *Staphylococcus aureus* Cowan I in the presence of a test compound. The level of inhibition of IL-12 production can be measured by determining the amount of p70 by using a sandwich ELISA assay with anti-human IL-12 antibodies. $IC_{50}$ of the test compound can then be determined. Specifically, PBMC or THP-1 cells are incubated with the test compound. Cell viability was assessed using the bioreduction of MTS [3-(4,5-dimethylthiazol-2-yl)-5-(3-carboxymethoxyphenyl)-2-(4-sulfophenyl)-2H-tetrazolium] (Promega, Madison, Wis.).

A disalt can also be evaluated by animal studies. For example, one of such studies involves the ability of a test compound to treat adjuvant arthritis (i.e., a IL-12 production related disorder) in rats.

Responsiveness of a particular condition, disease or disorder to disalts and compositions of this invention can be measured directly by comparison against conventional drugs, or can be inferred based on an understanding of disease etiology and progression. There are a number of cellular and bone resorption assay systems that are widely accepted in the art as predictive of in vivo effects. As the bone resorption assay uses material that includes all bone cells, it is an ex vivo assay. Thus, the showing that a disalt of this invention inhibits bone resorption in these assays is evidence of the clinical utility of these for treating or preventing conditions associated with excessive bone loss. Various scientific publications (such as Carano et al. J. Clin. Invest. 85: 456-461 (1990); Blair & Schlesinger, The Biology and Physiology of the Osteoclast, CRC Press, Eds., Gay, C. V. and Rifkin, B. R., pp. 259-288 (1992); and Vaananen et al., J. Cell Biology 111: 1305-1311 (1990)) support the fact that such assays are accepted as being predictive of in vivo activity. Furthermore, the in vitro effects of Herbimycin A on bone resorption were shown to correlate with in vivo activity (Yoneda et al., J. Clin. Invest. 91: 2791-95 (1993)).

Without further elaboration, it is believed that the above description has adequately enabled the present invention. The following specific embodiments are, therefore, to be construed as merely illustrative, and not limitative of the remainder of the disclosure in any way whatsoever. All of the publications cited herein are hereby incorporated by reference in their entirety.

EXAMPLES

Example 1

General Procedures for Disalt Formation

Procedure I. A stirred suspension of the IL-12 production inhibitor compound in absolute ethanol (in amount sufficient to obtain 0.33-0.34 M solution) is heated to 70° C. until all solids are dissolved. To the stirred, heated (solution was allowed to cool down to room temperature when hydrogen chloride solution in ether is used) solution an appropriate acid or solution thereof, 2 equivalents, is added portionwise (dropwise if liquid or solution and in 4-5 portions if solid), heating (65-70° C.). The solution is stirred for an additional 2 minutes, and then is allowed to cool to room temperature and is allowed to stand during precipitation of the disalt at room temperature for 2 hours or until precipitation of the disalt was complete. In instances when precipitation is slow or difficult, stirring often facilitates precipitation. The disalt is filtered, washed with two portions of anhydrous ethanol:ethyl ether 1:2 mixture and then with anhydrous ethyl ether, and is immediately (to minimize the possibility of solvent occlusion) vacuum-dried (ca. 2 mm Hg) at 50-60° C. (water bath) for about 45 minutes to 2 hours (drying is continued until the disalt achieves a constant weight and/or no ethanol is detected by $^1$H NMR). The disalt is then dried in vacuo further over a desiccant for an additional 2 hours at ca. 2 mm Hg over DRIERITE or phosphorous pentoxide. The disalts are generally colorless solids and are stored in the light-protected bottles.

Procedure II. A stirred suspension of the IL-12 production inhibitor compound in a solvent or mixed solvent system (absolute ethanol, mixture of absolute ethanol and toluene (1:1), or mixture of absolute ethanol and chloroform (1:1) is heated to 70° C. until all solids are dissolved. To the stirred, hot solution is added dropwise 2 equivalents of methane sulfonic acid. Heating (65-70° C.) and stirring is continued for 2 min, and the resultant solution is left at room temperature for precipitation (in those instances in which chloroform is used, the chloroform was removed under reduced pressure and equal amount of toluene was added to achieve precipitation). The disalt is filtered, washed with two portions of anhydrous ethanol:ether (1:2) then with anhydrous ether, and immediately vacuum-dried at 50-60° C. (water bath) for 2 hours to afford corresponding dimesylates. The disalt is then dried in vacuo further over a desiccant for an additional 2 hours at ca. 2 mmHg over DRIERITE or phosphorous pentoxide. The disalts are generally colorless solids and are stored in the light-protected bottles.

Procedure III. Alternatively, an ethanol suspension of the IL-12 production inhibitor compound is treated with 2 equivalents of methane sulfonic acid and stirred at room temperature until all solids dissolved. Disalt formation is then carried out as described above.

Example 2

N-(1H-indol-3-ylmethylene)—N'-[6-morpholin-4-yl-2-(2-pyridin-2-yl-ethoxy)-pyrimidin-4-yl]-hydrazine (2) dimethanesulfonate (dimesylate), $\{[(2)(2H^+)]^{2+}\cdot[2(CH_3SO_3^-)]^{2-}\}$.

A stirred suspension of 2, 0.683 g (1.54 mmol) in 10 mL of absolute ethanol was heated to 70° C. Methanesulfonic acid, 0.2 mL (3.08 mmol) was added dropwise to the stirred hot suspension, and heating (65-70° C.) and stirring was continued for an additional 2 minutes. The resultant solution was left at room temperature for 4 hours. The disalt was filtered, washed with two portions of anhydrous ethanol:ether (1:2) and then with anhydrous ether. The disalt was immediately vacuum-dried at 50-60° C. (water bath) for 2 hours to afford $\{[(2)(2H^+)]^{2+}\cdot[2(CH_3SO_3^-)]^{2-}\}$, 0.91 g (93%), as a colorless solid; melting point 160-165° C. $^1$H NMR (DMSO-$d_6$):δ 11.61 (s, 1H), 10.99 (brs, 1H), 8.85 (d, J=6.0 Hz, 1H), 8.47 (t, J=7.2 Hz, 1H), 8.31 (s, 1H), 8.18 (d, J=6.9 Hz, 1H),), 8.01 (d, J=8.1 Hz, 1H), 7.88 (t, J=6.6 Hz, 1H), 7.83 (s, 1H), 7.44 (d, J=8.1 Hz, 1H), 7.23-7.17 (m, 2H), 5.97 (s, 1H), 4.74 (m, 2H), 3.72 (m, 4H), 3.59 (m, 4H), 3.46(t, J=5.7 Hz, 2H), 2.36 (s, 6H). Anal. Calcd for $C_{26}H_{33}N_7O_8S_2$+$H_2O$: C, 47.77; H, 5.40; N, 15.00; O, 22.03; S, 9.81. Found: C, 47.94; H, 5.23; N, 14.99; O, 21.87; S, 9.89.

Example 3

N'-(1H-indol-3-ylmethylene)-N-methyl-N-[6-morpholin-4-yl-2-(2-pyridin-2-yl-ethoxy)-pyrimidin-4-yl]-hydrazine (3) dimesylate,

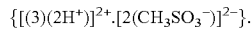

A stirred suspension of 3, 0.611 g (1.54 mmol) in 7.5 mL of absolute ethanol was heated to 70 ° C. Methanesulfonic acid, 0.2 mL (3.08 mmol) was added dropwise to the stirred hot suspension, and heating (65-70 ° C.) and stirring was continued for an additional 2 minutes. The resultant solution was left at room temperature for 4 hours. The disalt was filtered, washed with two portions of anhydrous ethanol:ether (1:2) and then with anhydrous ether, and then immediately vacuum-dried at 50-60 ° C. (water bath) for 2 hours to afford $\{[(3)(2H^+)]^{2+}\cdot[2(CH_3SO_3^-)]^{2-}\}$, 0.83 g (83%), as a light-yellow solid; melting point 130-140 ° C. $^1$H NMR (DMSO-$d_6$): δ 11.52 (s, 1H), 8.88 (d, J=5.1 Hz, 1H), 8.55 (t, J=8.4 Hz, 1H), 8.21 (s, 1H), 8.18 (d, J=7.2 Hz, 1H), ), 8.10 (d, J=8.1 Hz, 1H), 7.95 (t, J=6.6 Hz, 1H), 7.81 (d, J=2.4 Hz, 1H), 7.46 (d, J=7.2 Hz, 1H), 7.22-7.16 (m, 2H), 6.41(s, 1H), 4.72 (t, J=6.0 Hz, 2H), 3.72 (m, 4H), 3.51-3.48 (m, 7H), 3.47(t, J=5.1 Hz, 2H), 2.36 (s, 6H). Anal. Calcd for $C_{27}H_{35}N_7O_8S_2$+$1.25H_2O$: C, 48.3 1; H, 5.48; N, 14.61; O, 22.05; S, 9.55. Found: C, 48.17; H, 5.41; N, 14.34; O, 22.40; S, 9.68.

Example 4

N-(3-Methyl-benzylidene)—N!-[6-morpholin-4-yl-2-(2-morpholin-4-yl-ethoxy)-pyrimidin-4-yl]-hydrazine (4) dimesylate, $\{[(4)(2H^+)]^{2+}\cdot[2(CH_3SO_3^{31})]^{2-}\}$.

A stirred suspension of 4, 0.263 g (0.62 mmol) in 2 mL of toluene was heated to 70° C. until all solids were dissolved. Methanesulfonic acid, 0.08 mL (1.24 mmol) was added dropwise to the stirred hot solution, and heating (65-70° C.) and stirring was continued for an additional 2 minutes. The resultant solution was left at room temperature for 4 hours. The disalt was filtered, washed with two portions of anhydrous ethanol:ether (1:2) and then with anhydrous ether, and immediately vacuum-dried at 50-60° C. (water bath) for 2 hours to afford $\{[(4)(2H^+)]^{2+}\cdot[2(CH_3SO_3^-)]^{2-}\}$, 0.36 g (94%), as a colorless solid, melting point 215-219° C. $^1$H NMR (DMSO-$d_6$): δ 11.18 (brs, 1H), 9.98 (brs, 1H), 8.06 (s, 1H), 7.56-7.54 (m, 2H), 7.29 (t, J=7.8 Hz, 1H), 7.20 (t, J=7.5 Hz, 1H), 6.09 (s, 1H), 4.62 (m, 2H), 3.92 (m, 8H), 3.69 (m, 4H), 3.60 (m, 4H), 3.20 (m, 2H), 2.37 (s, 6H), 2.34(s, 3H). Anal. Calcd for $C_{24}H_{37}N_6O_{10}S_2$+$H_2O$: C, 45.34; H, 6.18; N, 13.22; O, 25.17; S, 10.09. Found: C, 45.49; H, 6.00; N, 13.25; O, 24.90; S, 10.36.

Example 5

N-(3-Methyl-benzylidene)—N'-[4-morpholin-4-yl-6-(pyridin-2-yl-ethoxy)-[1,3,5]-triazin-2-yl]-hydrazine (5) dimesylate,

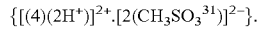

A stirred suspension of 5, 0.516 g (1.23 mmol) in a mixture of 2.0 mL of absolute ethanol and 2.0 mL of toluene was heated to 70° C. until all solids were dissolved. Methanesulfonic acid, 0.16 mL (2.46mmol) was added dropwise to the stirred hot solution, and heating (65-70° C.) and stirring was continued for an additional two 2 minutes. The resultant solution was left at room temperature for 4 hours. The disalt was filtered, washed with two portions of anhydrous ethanol: ether (1:2) and then with anhydrous ether, and immediately vacuum-dried at 50-60° C. (water bath) for 2 hours to afford $\{[(5)(2H^+)]^{2+}\cdot[2(CH_3SO_3^-)]^{2-}\}$, 0.707 g (94%), as a colorless solid; melting point 143-147° C. $^1$H NMR (DMSO-$d_6$): δ 11.78 (brs, 1H), 11.18 (brs, 1H), 8.87 (d, J=5.7 Hz, 1H), 8.52 (t, J=8.4 Hz, 1H), 8.10-8.06 (m, 2H), 7.93 (t, J=6.3 Hz, 1H), 7.53 (m, 2H), 7.32 (t, J=6.3 Hz, 1H), 6.09 (s, 1H), 4.62 (m, 2H), 3.92 (m, 8H), 3.69 (m, 4H), 3.60 (m, 4H), 3.20 (m, 2H), 2.37 (s, 6H), 2.34(s, 3H). Anal. Calcd for $C_{24}H_{33}N_7O_8S_2$+$2.25H_2O$+$0.25$ $MeSO_3H$: C, 43.35; H, 5.74; N, 14.62; S, 10.52. Found: C, 43.32; H, 5.55; N, 14.51; S, 10.31.

Example 6

N-(1H-Indol-3-ylmethylene)-N'-[4-morpholin-4-yl-6-(2-pyridin-2-yl-ethoxy)-[1,3,5]-triazin-2-yl]-hydrazine (6) dimesylate,

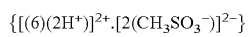

A stirred suspension of 6, 1.37 g (3.08 mmol) in 20 mL of absolute ethanol was heated to 70° C. Methanesulfonic acid, 0.4 mL (6.16 mmol) was added dropwise to the stirred hot suspension, and heating (65-70° C.) and stirring was continued for an additional 2 minutes. The resultant solution was left at room temperature for 4 hours. The disalt was filtered, washed with two portions of anhydrous ethanol:ether (1) and then with anhydrous ether, and immediately vacuum-dried at 50-60° C. (water bath) for 2 hours to afford $\{[(6)(2H^+)]^{2+}\cdot[2(CH_3SO_3^-)]^{2-}\}$, 1.61 g (82%), as an off-white solid; melting point 158-161° C. $^1$HNMR(DMSO-$d_6$): δ 11.60-11.46(brm, 2H), 8.87 (d, J=3.8 Hz, 1H), 8.50 (m, 1H), 8.35-8.30 (m, 2H), 8.07 (d, J=7.2 Hz, 1H), 7.92 (m, 1H), 7.81-7.78 (m, 1H), 7.42 (d, J=8.1 Hz, 1H), 7.12 (m, 1H), 7.09 (t, J=7.5 Hz, 1H), 4.86 (m, 1H), 4.68 (m, 1H), 3.74 (m, 4H), 3.66 (m, 4H), 3.47-3.43 (m, 2H), 2.35 (s, 6H). Anal. Calcd for $C_{25}H_{31}N_8O_8S_2$+$1.25H_2O$: C, 4845.62; H, 5.13; N, 17.02; 0, 22.48; S, 9.74. Found: C, 45.54; H, 5.16; N, 16.77; 0, 22.51; S, 10.02.

Example 7

[7-Morpholin-4-yl-5-(2-pyridin-2-yl-ethoxy)-3H-[1,2,4]-triazolo[1,5-a] [1,3,5]-triazin-2-yl]-m-tolyl-amine (7) dimesylate,

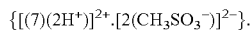

A stirred suspension of 7, 0.332 g (0.15 mmol) in 2 mL of absolute ethanol was heated to 70° C. Methanesulfonic acid, 0.02 mL (0.3 mmol) was added dropwise to the stirred hot suspension, and heating (65-70° C.) and stirring continued for an additional 2 minutes. The resultant solution was cooled and then concentrated to leave the minimum amount of solvent. To the resultant solution, toluene, 1 mL, was added, and the solvent gently distilled until precipitation started, or until about 0.5 mL of ethanol remained. The mixture was left at room temperature for 4 hours. The disalt was filtered, washed with two portions of anhydrous ethanol:ether (1:2) and then with anhydrous ether, and immediately vacuum-dried at 50-60° C. (water bath) for 2 hours to afford $\{[(7)(2H^+)]^{2+}\cdot[2(CH_3SO_3^-)]^{2-}\}$; 0.45 g (94%), as an off-white solid, melting point 137-141° C. $^1$H NMR (DMSO-$d_6$): δ 9.58 (brs, 1H), 8.84 (d, J=5.1 Hz, 1H), 8.47 (t, J=7.1 Hz, 1H), 8.02 (d, J=7.8

Hz, 1H), 7.89 (t, J=7.6 Hz, 1H), 7.41 (s, 1H), 7.37 (d, J=8.4 Hz, 1H), 7.18 (t, J=7.8 Hz, 1H), 6.79 (t, J=7.2 Hz, 1H), 4.70 (m, 2H), 3.99 (m, 4H), 3.73 (m, 4H), 3.45 (t, J=5.7 Hz, 2H), 2.37 (s, 6H), 2.27 (s, 3H).

Example 8

N-(3-Methyl-benzylidene)-N'-[6-morpholin-4-yl-2-(2-pyridin-2-yl-ethoxy)-pyrimidin-4-yl]-hydrazine (1) dimethanesulfonate (dimesylate),

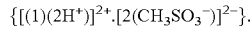

$\{[(1)(2H^+)]^{2+}\cdot[2(CH_3SO_3^-)]^{2-}\}$.

Procedure 1: A stirred suspension of 1, 11.3 g (27 mmol) in 80 mL of absolute ethanol was heated to 70° C. until all solids were dissolved. Methanesulfonic acid, 3.5 mL (54 mmol) was added dropwise to the stirred hot solution, and heating (65-70° C.) and stirring was continued for 2 minutes. The resultant solution was left at room temperature for 2 hours (precipitation started soon, slowly, within ca. 5 minutes). The disalt was filtered, washed with two portions of anhydrous ethanol:ether (1:2) (18, 36 mL) and then with 26 mL of anhydrous ether, and immediately vacuum-dried at 50-60° C. (water bath) for 2 hours, followed by vacuum-drying over a desiccant for 2 hours to afford $\{[(1)(2H^+)]^{2+}\cdot[2(CH_3SO_3^-)]^{2-}\}$, 16.1 g (97.6%), as a colorless solid, melting point 194-195° C. $^1$H NMR (DMSO-$d_6$): δ 8.86 (d, J=5.4 Hz, 1H), 8.51 (t, J=7.8 Hz, 1H), 8.05 (m, 1H), 8.04 (s, 1H), 7.92 (t, J=6.0 Hz, 1H), 7.59-7.55 (m, 2H), 7.31 (t, J=7.5 Hz, 1H), 7.21 (d, J=7.5 Hz, 1H), 6.02 (s, 1H), 4.71 (m, 2H), 3.68 (m, 4H), 3.58 (m, 4H), 3.47 (t, J=6.9 Hz, 2H), 2.37 (s, 3H), 2.36 (s, 3H), 2.34 (s, 3H). Anal. Calcd for $C_{25}H_{34}N_6O_8S_2$: C, 49.17; H, 5.61; N, 13.76; O, 20.96; S, 10.50. Found: C, 49.24; H, 5.63; N, 13.63; O, 20.80; S, 10.56. % $H_2O$ was 0.11%.

Procedure 2: Compound 1, (548.1 mg, 1.3 mmol) was dissolved in a mixture of toluene (6 mL) and absolute ethanol (0.5 mL) by stirring at room temperature. To the stirred solution methanesulfonic acid, (0.17 mL, 2 eq) was added. Precipitation of the salt started soon after addition of the methanesulfonic acid. The slurry was stirred for 2 hours to complete precipitation, the solid was filtered out, washed two times with absolute ethanol, and vacuum-dried to remove the residues of solvents. N-(3-methyl-benzylidene)-N'-[6-morpholin-4-yl-2-(2-pyridin-2-yl-ethoxy)-pyrimidin-4-yl]-hydrazine dimethanesulfonate was obtained in 98%, with $^1$H NMR, m.p., and elemental analysis as given above.

This procedure is less exothermic than procedure I. Procedure II may alternatively be carried out by dissolving the methanesulfonic acid in absolute ethanol before adding it to the toluene/ethanol solution of 1. Methanol and 1-butanol may be substituted for ethanol in Procedure II.

Procedure III. Compound 1, (548.1 mg, 1.3 mmol) was dissolved in absolute ethanol (8 mL) by heating to 75° C. To the stirred solution at that temperature methanesulfonic acid, (0.17 mL, 2 eq) in water (from 0.17 to 0.2 mL) was added. After addition, the stirring turned off, and the resulted clear solution was slowly cooled to room temperature (within 3.5-4 hours). Precipitation of the salt started at around 35° C. Reaction mixture was left overnight to complete precipitation. The solid was filtered out, washed two times with absolute ethanol, then once with ethyl ether and vacuum-dried to remove the residues of solvents. N-(3-methyl-benzylidene)-N'-[6-morpholin-4-yl-2-(2-pyridin-2-yl-ethoxy)-pyrimidin-4-yl]-hydrazine dimethanesulfonate was obtained in 85%, with $^1$H NMR, m.p., and elemental analysis as given above. Procedure III yielded agglomerated material.

Procedure IV. Compound 1, (548.1 mg, 1.3 mmol) was dissolved in DMF (1 mL) by heating to 71° C. To the stirred hot solution methanesulfonic acid, (0.17 mL, 2 eq) in water (0.2 mL) was added. After the addition was complete, the stirring and heating were turned off, and the resulted clear solution was allowed to cool to room temperature (within 3.5-4 hours). Precipitation of the salt started at around 43° C. Reaction mixture was left overnight to complete precipitation. The solid was filtered out, washed two times with absolute ethanol, then once with ethyl ether and vacuum-dried to remove the residues of solvents. N-(3-methyl-benzylidene)-N'-[6-morpholin-4-yl-2-(2-pyridin-2-yl-ethoxy)-pyrimidin-4-yl]-hydrazine dimethanesulfonate was obtained in 85%, with $^1$H NMR, m.p., and elemental analysis as given above.

Recrystallization Procedure I. N-(3-methyl-benzylidene)-N'-[6-morpholin-4-yl-2-(2-pyridin-2-yl-ethoxy)-pyrimidin-4-yl]-hydrazine dimethanesulfonate (6 g, 9.8 mmol)) in 2.8 mL of purified water was stirred at 50° C. to achieve a clear solution. To the solution absolute ethanol, 28 mL, was added, and the resulted solution was allowed to cool to room temperature without stirring, and left overnight to complete the precipitation. The agglomerated solid was filtered out, washed twice with ethanol (10+10 mL), then once with ethyl ether (25 mL), and vacuum-dried to remove the residues of solvents. Yield 78%.

Recrystallization Procedure II. N-(3-methyl-benzylidene)-N'-[6-morpholin-4-yl-2-(2-pyridin-2-yl-ethoxy)-pyrimidin-4-yl]-hydrazine dimethanesulfonate (7.4 g, 12 mmol)) was dissolved in a mixture of purified water (5.4 mL) and 1-butanol (208.5 mL) by stirring at 70° C. After a clear solution was achieved, heating and stirring were turned off, and solution was left overnight for precipitation to be completed. The agglomerated solid was filtered out, washed twice with ethanol (20+20 mL), then once with ethyl ether (30 mL), and vacuum-dried to remove the residues of solvents. Yield 76%.

Example 9

N-(3-Methyl-benzylidene)-N'-[6-morpholin-4-yl-2-(2-pyridin-2-yl-ethoxy)-pyrimidin-4-yl]-hydrazine (1) dihydrogenchloride (dichloride),

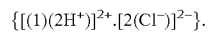

$\{[(1)(2H^+)]^{2+}\cdot[2(Cl^-)]^{2-}\}$.

Procedure I. A stirred suspension of 1, 7.7 g (18.4 mmol) in 65 mL of absolute ethanol was heated to 65-70° C. until everything dissolved. Into a stirred warm solution dry HCl gas was bubbled slowly. Some precipitate started to form; then flow of gas was increased and a clear solution was achieved. Bubbling continued until solution turned pale again, and precipitation started; the resulted solution was left for precipitation to be completed for 2 hours. The salt was filtered out, washed with two portions of anhydrous ethanol: ether 1:2 mixture (12: 24 mL), then with 16 mL of anhydrous ether and immediately vacuum-dried at 50-60° C. (water bath) for 2 hours, followed by vacuum-drying over the desiccant for 2 hours to afford 1 dihydrochloride, 8.3 (88%), colorless to off-white solid, melting point 171-173° C.(decompos).

$^1$H NMR (DMSO-$d_6$): δ 8.85 (d, J=5.4 Hz, 1H), 8.50 (td, J=8.1 and 1.5 Hz, 1H), 8.09 (s, 1H), 8.04 (d, J=8.4 Hz, 1H), 7.91 (t, J=7.2 Hz, 1H), 7.59-7.55 (m, 2H), 7.31 (t, J=7.5 Hz, 1H), 7.21 (d, J=7.8 Hz, 1H), 6.01 (s, 1H), 4.79 (m, 2H), 3.68 (m, 4H), 3.59 (m, 6H), 2.34 (s, 3H). Anal. Calcd for $C_{23}H_{28}Cl_2N_6O_2$+1 $H_2O$: C, 54.23; H, 5.94; Cl, 13.92; N, 16.50. Found: C, 54.08; H, 5.93; Cl, 13.81; N, 16.26.

Procedure II. A stirred suspension of 1, 2.51 g (6 mmol) in 30 mL of absolute ethanol was heated to 65-70° C. until everything dissolved. The stirred solution was allowed to cool down to room temperature, and a 2.0 M solution of hydrogen chloride in ether, 6.01 mL (12 mmol), was added dropwise.

The stirring continued for 2 min, and the resulted solution was left at room temperature for precipitation for 2 hours. The salt was filtered out, washed with two portions of anhydrous ethanol:ether 1:2 mixture (1.8: 3.6 mL), then with 3 mL of anhydrous ether and immediately vacuum-dried at 50-60° C. (water bath) for 2 hours, followed by vacuum-drying over the desiccant for 2 hours to afford 1 dihydrochloride, 2.2 g (72%), colorless to off-white solid.

$^1$H NMR (DMSO-d$_6$): δ 8.85 (d, J=5.4 Hz, 1H), 8.53 (td, J=8.1 and 1.5 Hz, 1H), 8.12 (s, 1H), 8.07 (d, J=8.4 Hz, 1H), 7.93 (t, J=7.2 Hz, 1H), 7.60 (m, 2H), 7.31 (t, J=7.5 Hz, 1H), 7.21 (d, J=7.8 Hz, 1H), 6.02 (s, 1H), 4.79 (m, 2H), 3.68 (m, 4H), 3.59 (m, 6H), 2.34 (s, 3H).

Example 10

N-(3-Methyl-benzylidene)-N'-[6-morpholin-4-yl-2-(2-pyridin-2-yl-ethoxy)-pyrimidin-4-yl]-hydrazine (1) dinitrate,

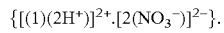

A stirred suspension of 1, 1.13 g (2.7 mmol) in a mixture of 9.3 mL of absolute ethanol was heated to 70° C. until all solids were dissolved. To the stirred, hot solution was added dropwise a solution of 70% nitric acid, 0.49 g (5.4 mmol) in 3.7 mL of absolute ethanol. Stirring was continued for an additional 2 minutes. The resultant solution was left at room temperature for 2 hours. The disalt was filtered, washed with two portions of anhydrous ethanol:ether (1:2) (1.8:3.6 mL) and then with 2.6 mL of anhydrous ether, and immediately vacuum-dried at 50-60° C. (water bath) for 2 hours, followed by vacuum-drying over the desiccant for 2 hours to afford {[(1)(2H$^+$)]$^{2+}$.[2(NO$_3^-$)]$^{2-}$}, 1.41g (97%), as a colorless solid; melting point 144-145° C. $^1$H NMR (DMSO-d$_6$): δ 8.86 (d, J=5.4 Hz, 1H), 8.50 (td, J=8.1 and 1.5 Hz, 1H), 8.08 (d, J=8.4 Hz, 1H), 8.05 (s, 1H), 7.92 (t, J=7.2 Hz, 1H), 7.60-7.56 (m, 2H), 7.31 (t, J=7.5 Hz, 1H), 7.19 (d, J=7.8 Hz, 1H), 6.01 (s, 1H), 4.71 (m, 2H), 3.70 (m, 4H), 3.59 (m, 4H), 3.45 (m, 2H), 2.34 (s, 3H). Anal. Calcd for C$_{23}$H$_{28}$N$_8$O$_8$: C, 50.73; H, 5.18; N, 20.58; O, 23.51. Found: C, 50.78; H, 5.08; N, 20.35; 0, 23.79.

Compound 1 can occlude solvents rapidly; therefore disalts prepared from compound 1 were vacuum dried immediately after isolation.

$^1$H NMR spectra of compound 1 disalts shows that the signals of two pyridine protons significantly shifted to the lower field; from 8.53 and 7.78 ppm for corresponding protons in the parent compound (1) to 8.85 and 8.40 ppm for the protons in disalts.

Satisfactory elemental analyses were obtained for disalts. In the case of dihydrogenhalogenides, however, water content was found to be about 3%.

Table 1 summarizes the behaviour of representative compounds 1-14 under disalt formation conditions described herein.

TABLE 1

| Compound | Acid | PKa | Result |
|---|---|---|---|
| 1 | CH$_3$SO$_3$H | −1.2 | Formed disalt, {[(1)(2H$^+$)]$^{2+}$•[2(CH$_3$SO$_3^-$)]$^{2-}$} |
| 1 | HCl | −4.5 | Formed disalt, {[(1)(2H$^+$)]$^{2+}$•[2(Cl$^-$)]$^{2-}$} |
| 1 | HBr | −7 | Formed disalt, {[(1)(2H$^+$)]$^{2+}$•[2(Br$^-$)]$^{2-}$} |
| 1 | HNO3 | −1.32 | Formed disalt, {[(1)(2H$^+$)]$^{2+}$•[2(NO$_3^-$)]$^{2-}$} |
| 1 | H$_2$SO$_4$ | −3 | Formed disalt, {[(1)(2H$^+$)]$^{2+}$•[2(HSO$_4^-$)]$^{2-}$} |
| 1 | PhSO$_3$H | 0.7 | Formed disalt, {[(1)(2H$^+$)]$^{2+}$•[2(PhSO$_3^-$)]$^{2-}$} |
| 1 | p-TolSO$_3$H | −1.34 | Formed disalt, {[(1)(2H$^+$)]$^{2+}$•[2(p-TolSO$_3^-$)]$^{2-}$} |
| 2 | CH$_3$SO$_3$H | −1.2 | Formed disalt, {[(2)(2H$^+$)]$^{2+}$•[2(CH$_3$SO$_3^-$)]$^{2-}$} |
| 3 | CH$_3$SO$_3$H | −1.2 | Formed disalt, {[(3)(2H$^+$)]$^{2+}$•[2(CH$_3$SO$_3^-$)]$^{2-}$} |
| 4 | CH$_3$SO$_3$H | −1.2 | Formed disalt, {[(4)(2H$^+$)]$^{2+}$•[2(CH$_3$SO$_3^-$)]$^{2-}$} |
| 5 | CH$_3$SO$_3$H | −1.2 | Formed disalt, {[(5)(2H$^+$)]$^{2+}$•[2(CH$_3$SO$_3^-$)]$^{2-}$} |
| 6 | CH$_3$SO$_3$H | −1.2 | Formed disalt, {[(6)(2H$^+$)]$^{2+}$•[2(CH$_3$SO$_3^-$)]$^{2-}$} |
| 7 | CH$_3$SO$_3$H | −1.2 | Formed disalt, {[(7)(2H$^+$)]$^{2+}$•[2(CH$_3$SO$_3^-$)]$^{2-}$} |
| 8 | CH$_3$SO$_3$H | −1.2 | Isolated mixture of disalt, {[(8)(2H$^+$)]$^{2+}$•[2(CH$_3$SO$_3^-$)]$^{2-}$}, and monosalt, {[(8)(1H$^+$)]$^{1+}$•[1(CH$_3$SO$_3^-$)]$^{1-}$} |
| 9 | CH$_3$SO$_3$H | −1.2 | Formed disalt, {[(9)(2H$^+$)]$^{2+}$•[2(CH$_3$SO$_3^-$)]$^{2-}$} |
| 10 | CH$_3$SO$_3$H | −1.2 | Formed disalt, {[(10)(2H$^+$)]$^{2+}$•[2(CH$_3$SO$_3^-$)]$^{2-}$} |
| 11 | CH$_3$SO$_3$H | −1.2 | Formed monosalt only, {[(11)(1H$^+$)]$^{1+}$•[1(CH$_3$SO$_3^-$)]$^{1-}$} |
| 12 | CH$_3$SO$_3$H | −1.2 | Formed monosalt only, {[(12)(1H$^+$)]$^{1+}$•[1(CH$_3$SO$_3^-$)]$^{1-}$} |
| 13 | CH$_3$SO$_3$H | −1.2 | Formed monosalt only, {[(13)(2H$^+$)]$^{2+}$•[1(CH$_3$SO$_3^-$)]$^{1-}$} |
| 14 | CH$_3$SO$_3$H | −1.2 | No salt formation observed |

Disalt, {[(1)(2H$^+$)]$^{2+}$.[2(Cl$^-$)]$^{2-}$}, was determined to be soluble in water at a concentration of 5 mg/0.1 mL. This salt further contains about 3% water.

Disalt, {[(1)(2H$^+$)]$^{2+}$.[2(Br$^-$)]$^{2-}$}, was determined to have a melting point of 153-155° C. and to be soluble in water at a concentration of 5 mg/0.1 mL. This salt further contains about 3.1% water.

Disalt, {[(1)(2H$^+$)]$^{2+}$.[2(NO$_3^-$)]$^{2-}$}, was determined to have a melting point of 142-143° C. and to be insoluble in water at a concentration of 5 mg/0.1 mL and partially soluble in water at a concentrations of 5 mg/0.2 mL and 5 mg/0.25 mL.

Disalt, {[(1)(2H$^+$)]$^{2+}$.[2(HSO$_4^-$)]$^{2-}$} was determined to have a melting point of 127-130° C. and was soluble in water at concentrations of 5 mg/0.1 mL.

Disalt, {[(1)(2H$^+$)]$^{2+}$.[2(PhSO$_3^-$)]$^{2-}$} was determined to have a melting point of 194-195° C. and to be insoluble in water at a concentration of 5 mg/0.1 mL and partially soluble in water at a concentrations of 5 mg/0.2 mL and 5 mg/0.25 mL. This salt further contains about 0.11% water.

Disalt, $\{[(1)(2H^+)]^{2+} \cdot [2(p\text{-TolSO}_3^-)]^{2-}\}$ was determined to have a melting point of 179-181° C. and to be insoluble in water at a concentration of 5 mg/0.1 mL, partially soluble in water at a concentration of 5 mg/0.2 mL, and soluble in water with heating at a concentration of 5 mg/0.25 mL.

Example 11

Mono-Salts

N-(3-Methyl-benzylidene)-N'-[6-morpholin-4-yl-2-(2-pyridin-2-yl-ethoxy)-pyrimidin-4-yl]-hydrazine 1 methanesulfonate (mesylate)

A stirred suspension of 1, 2.51 g (6 mmol) in a mixture of 7.5 mL of absolute ethanol and 10 mL of toluene was heated to 70° C. until everything dissolved. To the stirred hot solution a methanesulfonic acid, 0.39 mL (6 mmol) was added dropwise, heating and stirring continued for 1 min, and the resulted solution was left at room temperature for precipitation (precipitation started soon, slowly) for 2 hours. The salt was filtered out, washed with two portions of absolute ethanol (4 mL), and vacuum-dried at 50-60° C. (water bath) for 2 hours to afford 1 mesylate 2.9 g (94%), colorless solid, melting point 162-163° C.

$^1$H NMR (DMSO-$d_6$): δ 11.07 (brs, 1H), 8.81 (d, J=5.7 Hz, 1H), 8.39 (t, J=7.8 Hz, 1H), 8.02 (s, 1H), 7.93 (d, J=8.1 Hz, 1H), 7.81 (t, J=6.6 Hz, 1H), 7.54-7.51 (m, 2H), 7.30 (t, J=7.8 Hz, 1H), 7.19 (d, J=7.5 Hz,1H), 6.04 (s, 1H), 4.65 (t, J=6.0 Hz, 2H), 3.67 (m, 4H), 3.55 (m, 4H), 3.39(m, 2H), 2.34 (s, 6H). Anal. Calcd for $C_{24}H_{30}N_6O_5S + \frac{2}{3}H_2O + \frac{2}{3}EtOH$: C, 54.60; H, 6.39; N, 15.08; S, 5.75. Found: C, 54.86; H, 6.14; N, 14.78; S, 5.99.

A stirred suspension of 1, 2.51 g (6 mmol) in 30 mL of absolute ethanol was heated to 65-70° C. until everything dissolved. To the stirred hot solution a methanesulfonic acid, 0.39 mL (6 mmol) was added dropwise, and stirring continued for 1 min, and the resulted solution was left at room temperature for precipitation (precipitation started in 2 min) for 45 min. The salt was filtered out, washed with of absolute ethanol (4 mL), than with anhydrous ether(4 ml), and vacuum-dried at 50-60° C (water bath) for 2 hours to afford 1 mesylate 3.08 g (99%), colorless solid, melting point 162-163° C.

N-(3-Methyl-benzylidene)-N'-[6-morpholin-4-yl-2-(2-pyridin-2-yl-ethoxy)-pyrimidin-4-yl]-hydrazine (1) hydrochloride A stirred suspension of 1, 2.51 g (6 mmol) in 30 mL of absolute ethanol was heated to 65-70° C. until everything dissolved. The stirred solution was allowed to cool down to room temperature, and a 2.0 M solution of hydrogen chloride in ether, 3.01 mL (6 mmol), was added dropwise. The stirring continued for 2 min, and the resulted solution was left at room temperature for precipitation for 2 hours. The salt was filtered out, washed with two portions of anhydrous ethanol:ether 1:2 mixture (1.8:3.6 mL), then with 3 mL of anhydrous ether and immediately vacuum-dried at 50-60° C. (water bath) for 1 hour to afford 1 hydrochloride, 2.04 g (75%), colorless to off-white solid, melting point 176-178° C.

$^1$H NMR (DMSO-$d_6$): δ 11.04 (brs, 1H), 8.77 (d, J=5.1 Hz, 1H), 8.34 (t, J=8.1 and 1.5 Hz, 1H), 8.02 (s, 1H), 7.88 (d, J=8.1 Hz, 1H), 7.77 (t, J=7.2 Hz, 1H), 7.54-7.51 (m, 2H), 7.30 (t, J=7.6 Hz, 1H), 7.18 (d, J=7.2 Hz, 1H), 6.04 (s, 1H), 4.64 (t, J=5.7 Hz, 2H), 3.67 (m, 4H), 3.54 (m, 4H), 3.42 (m, 2H), 2.34 (s, 3H). Anal. Calcd for $C_{23}H_{27}ClN_6O_2 + \frac{1}{4}H_2O$: C, 60.12; H, 6.03; N, 18.29; Cl, 7.72. Found: C, 60.39; H, 6.05; N, 18.03; Cl, 7.87.

Example 12

Solubility Determination

The compound was weighed, and water was added to it such that the ratio of the sample and water of the mixture would be 100 mg/mL. The mixture was then shaken using a Vortex-Genie2 shaker (vortexed) and sonicated (~5-10 min at ~50° C). If a clear solution has been obtained, more compound was added to the solution, and a mixture was vortexed and sonicated until a homogeneous suspension was achieved. The suspension was then centrifuged at 10,000 rpm for about 10 min. The supernatant was taken out and diluted with 50/50 (v/v) EtOH/water, then the sample was analyzed by HPLC to determine the concentration.

Instrumentation:

The HPLC system consisted of the HP 1100 Model (Agilent, Wilmington, Del.) equipped with a model 1100 quaternary pump, a model 1100 autosampler, a model 1100 Diode-Array Detector for UV detection at 320 nm. The HPLC analysis was performed using an isocratic mobile phase consisting of acetonitrile-water containing 10 mM $NH_4OAc$. Mobile phases were degassed and filtered through a solvent filtration apparatus and pumped at a constant rate of 1.0 mL/min. The separation was made on an XTerra MS C18 analytical column, 4.6 mm i.d.×150 mm, (Waters Corp., Milford, Mass., USA) fitted with a precolumn filter (XTerra MS C18, 3.9 mm×20mm). The column was maintained at 30° C. Data acquisition and instrument setting were controlled using HP Chemstation software (ver.8.03).

Table 2 summarizes the solubilities of various salts.

TABLE 2

| Salt | Solubility (mg/mL) |
| --- | --- |
| $\{[(1)(2H^+)]^{2+} \cdot [2(CH_3SO_3^-)]^{2-}\}$ | 831 +/− 5 |
| $\{[(1)(1H^+)]^{1+} \cdot [1(CH_3SO_3^-)]^{1-}\}$ | 52.0 +/− 0.1 |
| $\{[(1)(2H^+)]^{2+} \cdot [2(Cl^-)]^{2-}\}$ | 213 +/− 5 |
| $\{[(1)(1H^+)]^{1+} \cdot [1(Cl^-)]^{1-}\}$ | 12.6 +/− 0.4 |
| $\{[(1)(2H^+)]^{2+} \cdot [2(Br^-)]^{2-}\}$ | 246 +/− 3 |
| $\{[(1)(2H^+)]^{2+} \cdot [2(NO_3^-)]^{2-}\}$ | 83.4 +/− 0.2 |
| $\{[(1)(2H^+)]^{2+} \cdot [2(p\text{-TolSO}_3^-)]^{2-}\}$ | 12.1 +/− 0.1 |
| $\{[(1)(2H^+)]^{2+} \cdot [2(PhSO_3^-)]^{2-}\}$ | 14.6 +/− 0.0 |
| $\{[(3)(2H^+)]^{2+} \cdot [2(CH_3SO_3^-)]^{2-}\}$ | 306 +/− 14 |
| $\{[(2)(2H^+)]^{2+} \cdot [2(CH_3SO_3^-)]^{2-}\}$ | 454 +/− 5 |

The solubility of disalt $\{[(1)(2H^+)]^{2+} \cdot [2(CH_3SO_3^-)]^{2-}\}$ was, unexpectedly, more than ten times greater than the solubility of the corresponding monosalt, $\{[(1)(1H^+)]^{1+} \cdot [1(CH_3SO_3^-)]\}$. The solubilities of disalts of compound 1 having inorganic anionic charge balancing moieties were higher than the solubility of monosalt, $\{[(1)(1H^+)]^{1+} \cdot [1(CH_3SO_3^-)]^{1-}\}$. The solubilities of disalts of compounds 2 or 3 having mesylate anionic charge balancing moities were also higher than the solubility of monosalt, $\{[(1)(1H^+)]^{1+} \cdot [1(CH_3SO_3^-)]^{1-}\}$. Moreover, the disalts are less colored in appearance (indicating greater stability, less prone to decomposition) and appear to have lesser sensitivity to exposure to light (i.e., better light stability).

A number of embodiments of the invention have been described. Nevertheless, it will be understood that various modifications may be made without departing from the spirit and scope of the invention. Accordingly, other embodiments are within the scope of the following claim

What is claimed is:

1. A disalt represented by the formula:

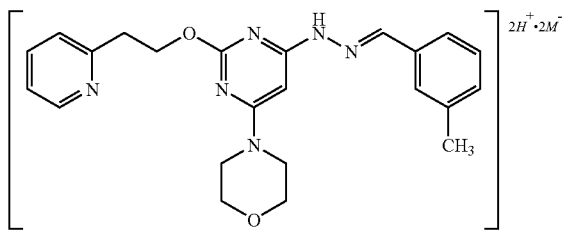

wherein each M⁻ is a conjugate base of a Bronsted acid.

2. The disalt of claim 1, wherein M⁻ is the conjugate base of a Bronsted acid selected from the group consisting of hydrochloric acid, nitric acid, sulfuric acid, hydrobromic acid, hydroiodic acid, perchloric acid, phosphoric acid, alkylsulfonic acids, arylsulfonic acids, halogenated alkylsulfonic acids, halogenated acetic acids, picric acid, oxalic acid, citric acid, formic acid, ascorbic acid and benzoic acid.

3. The disalt of claim 2, wherein M⁻ is methanesulfonate.

4. The disalt of claim 2, wherein M⁻ is bromide.

5. The disalt of claim 2, wherein M⁻ is chloride.

6. A pharmaceutical composition comprising a pharmaceutically acceptable carrier and a disalt according to claim 1.

* * * * *